United States Patent
Cormier et al.

(10) Patent No.: US 7,601,720 B2
(45) Date of Patent: Oct. 13, 2009

(54) NICOTINIC RECEPTOR AGONISTS FOR THE TREATMENT OF INFLAMMATORY DISEASES

(75) Inventors: Yvon Cormier, Neuville (CA); Evelyne Israel-Assayag, Sainte-Foy (CA); Marie-Renée Blanchet, St-Pierre Ile d'Orléans (CA)

(73) Assignee: Universite Laval, Quebec (CA)

( * ) Notice: Subject to any disclaimer, the term of this patent is extended or adjusted under 35 U.S.C. 154(b) by 649 days.

(21) Appl. No.: 10/469,999

(22) PCT Filed: Mar. 25, 2002

(86) PCT No.: PCT/CA02/00412

§ 371 (c)(1), (2), (4) Date: Feb. 24, 2004

(87) PCT Pub. No.: WO02/076434

PCT Pub. Date: Oct. 3, 2002

(65) Prior Publication Data

US 2004/0132737 A1    Jul. 8, 2004

(30) Foreign Application Priority Data

Mar. 23, 2001 (CA) .................................. 2341952

(51) Int. Cl.
*A61K 31/44* (2006.01)
*A61K 31/497* (2006.01)
*A61K 31/495* (2006.01)

(52) U.S. Cl. ............................ 514/252.12; 514/255.03; 514/392; 514/343

(58) Field of Classification Search ............ 514/252.12, 514/255.03, 343, 562, 392, 546
See application file for complete search history.

(56) References Cited

U.S. PATENT DOCUMENTS

| | | | |
|---|---|---|---|
| 2,778,772 | A | 1/1957 | Chen |
| 3,402,039 | A | 9/1968 | Mussell et al. |
| 5,846,983 | A | 12/1998 | Sandborn et al. |
| 5,977,144 | A | 11/1999 | Meyer et al. |
| 5,981,549 | A | 11/1999 | Viner |
| 6,177,429 | B1 | 1/2001 | Sit et al. |
| 6,610,713 | B2 | 8/2003 | Tracey |
| 6,838,471 | B2 | 1/2005 | Tracey |
| 2002/0151597 | A1* | 10/2002 | Banerjee et al. ............. 514/629 |
| 2002/0160988 | A1 | 10/2002 | Amitai et al. |
| 2004/0116519 | A1 | 6/2004 | Slatter |
| 2004/0132737 | A1 | 7/2004 | Cormier et al. |
| 2004/0132774 | A1 | 7/2004 | Heath |
| 2004/0138289 | A1 | 7/2004 | Richards et al. |
| 2004/0242569 | A1 | 12/2004 | Lennon et al. |
| 2004/0254373 | A1 | 12/2004 | Piotrowski et al. |
| 2005/0019271 | A1 | 1/2005 | Bannister et al. |
| 2005/0075323 | A1 | 4/2005 | Day et al. |
| 2005/0130990 | A1 | 6/2005 | Cormier et al. |

FOREIGN PATENT DOCUMENTS

| | | |
|---|---|---|
| EP | 1462091 | 9/2004 |
| JP | 2003/176240 A | 6/2003 |
| WO | WO96/15117 * | 5/1996 |
| WO | WO 98 02188 A | 1/1998 |
| WO | WO/99/21834 | 5/1999 |
| WO | WO 00 23062 A | 7/2000 |
| WO | WO 01 15697 A | 3/2001 |
| WO | WO 02 44176 A | 6/2002 |
| WO | WO/2002/076434 A2 | 10/2002 |
| WO | WO/2006/005195 | 1/2006 |

OTHER PUBLICATIONS

Migueres et al. Techniques of Desensitiazation. Revue des Maladies Respiratories, 1986 vol. 3, No. 1 pp. 39-44, abstract.*
Ikemori et al. Doctor-patient relationship in the treatment of bronchial ashtma. Japanese Journal of Psychosomatic Medicine, 1979 vol. 19, No. 5, pp. 359-364. (abstract).*
The Merck Manual, 16$^{th}$ Edition, pp. 658-659.*
Cormier, Y. et al. 1985, *Factors influencing the development of serum precipitins to farmer's lung antigen in Quebec dairy farmers*, Thorax 40(2): 138-142.
Cormier, Y. et al., 1988, *Sequential bronchoalveolar lavage in experimental extrinsic allergic alveolitis*. The influence of cigarette smoking, Am Rev Respir Dis 137(5): 1104-1109.
Cormier, Y. et al., 1998, *Hypersensitivity pneumonitis in peat moss processing plant workers*, Am J Respir. Crit Care Med 158(2): 412-417.

(Continued)

*Primary Examiner*—Jennifer Myong M Kim
(74) *Attorney, Agent, or Firm*—Buchanan Ingersoll & Rooney PC

(57) ABSTRACT

This invention relates to the use of nicotine receptor agonists for treating inflammatory diseases, including a variety of pulmonary diseases. Such agonists have fewer side effects than other anti-inflammatory drugs, such as steroids. Moreover, these agonists can be used alone or in combination with other anti-inflammatory drugs to alleviate pulmonary diseases.

7 Claims, 13 Drawing Sheets

OTHER PUBLICATIONS

Gariepy, L. et al., 1989, *Predictive value of bronchoalveolar lavage cells and serum precipitins in asymptomatic dairy farmers*, Am Rev Respir Dis. 140(5): 1386-1389.

Lawrence, E.C. et al., 1986, *Cigarette smoking and bronchoalveolar T Cell populations in sarcoidosis*, Ann NY Acad Sci 465:657-664.

Valeyre D. et al., 1988, *Smoking and pulmonary sarcoidosis: effect of cigarette smoking on prevalence, clinical manifestations, alveolitis, and evolution of the disease*, Thorax 43(7):516-524.

Rubin, D.T. and Hanuer, S. B., 2000, *Smoking and inflammatory bowel disease*. Eur J Gastroenterol Hepetol 12(8):855-862.

Thomas, G.A. et al., 2000, *Role of smoking in flammatory bowel disease : implications for therapy*. Postgrad Med J 76(895):273-279.

Guslandi, M., 1999, *Nicotine Treatment for ulcerative colitis. Br . Clin Pharmacol* 48(4):481-484.

Guslandi, M., 1999, *Long-term effects of a single course of nicotine treatment in acute ulcerative colitis:remission maintenance in a 12-month follow-up study*. Int J Colorectal Dis 14(4-5):261-262.

Rezvani, A.H. and Levin E.D., 2001, *Cognitive effects of nicotine*. Biol Psychiatry 49(3):258-267.

Kelton, M.C. et al., 2000, *The effects of nicotine in Parkinson's disease*. Brain Cogn 43(1-3):274-282.

Bertram, K.G., 1998, *Basic and clinical pharmacology*. Editions Appelton and Lange. Stanford. Connecticut.

Sekhon, H.S. et al., 1999, *Prenatal nicotine increases pulmonary alpha 7 nicotinic receptor expression and alters feta lung development in monkeys*. J Clin Invesst 103(5):637-647.

Maus, A.D. et al., 1998, *Human and rodent bronchial epithelial cells express functional nicotinic acetylcholine receptors*, Mol Pharmacol 54(5):779-788.

Shriver, S.P. et al., 2000, *Sex-specific expression of gastrin-releasing peptide receptor : relationship to smoking history and risk of lung cancer*. J Natl Cancer Inst. 92(1).

Ferguson, D.G. et al., 2000, *The alpha3 subtype of the nicotinic acetylcholine receptor is expressed in airway-related neurons of the nucleus tractus solitarius, but is not essential for reflex bronchoconstriction in ferrets*. Neurosci Lett 287(2):141-145.

Singh, S.P. et al., 2000, *Acute and chronic nicotine exposures modulate the immune system through different pathways*. Toxicol Appl Pharmacol 164(1): 65-72.

Kalra, R. et al., 2000, *Effects of cigarette smoke on immune response:chronic exposure to cigarette smoke impairs antigen-mediated signaling in T cells and depletes IP3-sensitive Ca(2+) stores*. J Pharmacol Exp Ther 293(1):166-171.

Sugano, N. et al., 1998, *Nicotine inhibits the production of inflammatory mediators in U937 cells through modulation of nuclear factor-kappaB activation,*. Biochem Biophys Res Commun 252(1):25-28.

Yates, S.L. et al., 1995, *Up-regulation of nicotinic acetycholine receptors following chronic exposure of rats to mainstream cigarette smoke or alpha 4 beta 2 receptors to nicotine*. Biochem Pharmacol 50(12):2001-2008.

Sopori, M.L. and Kosak W., 1998, *Immunomodulatory effects of cigarette smoke*. J Neuroimmunol 83(1-2):148-156.

Lahmouzi, J. et al., 2000, *Effect of nicotine on rat gingival fibroblasts in vitro*. Connect Tissue Res 41(1):69-80.

Geng, Y. et al., 1996, *Effects of nicotine on the immune response. II. Chronic nicotine treatment induces T cell anergy*, J Immunol 156(7):2384-2390.

McCrea, K.A. et al., 1994, *Altered cytokine regulation in the lungs of cigarette smokers*, Am J Respir Crit Care Med 150(3):696-703.

Ohta, T. et al., 1998, *Cigarette smoking decreases interleukin-8 secretion by human alveolar macrophages*, Respir. Med. 92(7):922-7.

Suzuki, N. et al., 1999, *Effects of cigarette smoking on Fas/Fas ligand expression of human lympocytes*. Cell Immunol 192(1):48-53.

Zia, S. et al., 1997, *Nicotine enhances expression of the alpha 3, alpha 4, alpha 5, and alpha 7 nicotinic receptors modulating calcium metabolism and regulating adhesion and motility of respiratory epithelial cells,*. Res Commun Mol Pathol Pharmacol 97(3):243-262.

Zhang, S. and Petro T.M.., 1996, *The effects of nicotine on murine CD4 T cell responses*. Int J Immunopharmacol 18(8-9):467-478.

Bugeon, L and Dallman J., 2000, *Constimulation of T cells*. Am J Respir Crit Care Med 162(4 Pt 2): S164-168.

Green, J.M., 2000, *The B7/CD28/CTLA4 T-cell activation pathway. Implications for inflammatory lung disease*. Am. J. Respir. Cell. Mol. Biol. 22(3):261-264.

Lenschow, D.J. et al., 1996 *CD28/B7 system of T cell costimulation*. Annu Rev. Immunol. 14:233-258.

Walunas, T.L. and Bluestone J.A., 1998, *CTLA-4 regulates tolerance induction and T cell differentiation in vivo*. J Immunol 160(8):3855-3860.

Walunas, T.L. et al., 1994, *CTLA-4 can function as a negative regulator of T cell activation*. Immunity 1(5):405-413.

Israel-Assayag, E. et al., 1999, *Expression of costimulatory molecules on alveolar macrophages in hypersensitivity pneumonitis*, Am J Respir Crit Care Med 159(6): 1830-1834.

Israel-Assayag E. et al., 1999, *Blockade of T cell constimulation by CTLA4-Ig inhibits lung inflammation in murine hypersensitivity pneumonitis*, J Immunol 163(12): 6794-6799.

Larche, M. et al., 1998, *Costimulation throuth CD86 is involved in airwat antigen-presenting cell and T cell responses to allergen in atopic asthmatics*, J Immunol 161(11):6375-6382.

Mathur, M. et al., 1999, *CD28 interactions with either CD80 or CD86 are sufficient to induce allergic airway inflammation in mice*. Am J Respir Cell Mol Biol 21(4):498-509.

Nicod, L.P. and Isler, P., 1997, *Alveolar macrophages in sarcoidosis coexpress high levels of CD86 (B7.2), CD40, and CD30L*. Am J Respir Cell Mol Biol 17(1):91-6.

Kesingland, A.C. et al., 2000, *Analgesic profile of the nicotinic acetylcholine receptor agonists, (+)-epibatidine and ABT-594 in models of persistent inflammatory and neuropahtic pain*, Pain 86(1-2):113-118.

Mellon, R.D. and Bayer B.M., 1999, *The effets of morphine, nicotine and epibatidine on lymphocyte activity and hypothalamic-pituitary-adrenal axis responses*, J Pharmacol Exp Ther 288(2):635-642.

Yokotani, K. et al., 2000, *Characterization of nicotinic acetylcholine receptor-mediated noradrenaline release fron the isolated rat stomach*, Eur J Pharmacol 402(3):223-9.

Yost, C.S. and Winegar B.D., 1997, *Potency of agonists and competitive antagonists on adult-and-fetal-type nicotinic acetyicholine receptors*, Cell Mol Neurobiol 17(1):35-50.

Fecho, K. et al., 1993, *Alterations of immune status induced by the sympathetic nervoux syatem: immunomodulatory effects of DMPP alone and in combination with morphine*, Brain Behav. Immun 7(3): 253-270.

Thompson D. et al., 1990, *Nicotinic agonist modulation of feline bronchomotor tone*, Clin Exp Pharmacol Physiol 17(2):83-97.

Barnes P.J., 2001, *Future Advances in COPD Therapy*, Respiration 68(5):441-448.

Lasky J.A. and Ortiz, L.A., 2001, *Antifibrotic therapy for the treatment of pulmonary fibrosis*, Am J Med Sci 322(4): 213-221.

Baron P.J., 1996, *Beneficial effecos of nicotine and cigarette smoking: the real, the possible and the spurious*, Br Med Bull 52(1): 58-73.

Waldum, H.L. et al., 1996, *Long-term effects of inhaled nicotine*, Life Sci 58(16) 1339-1346.

Warren, C. P., 1977, *Extrinsic allergic alveolitis: a disease commoner in non-smokers*, Thorax 32(5): 567-569.

Cormier, Y. et al., 1994, *Long-term viral enhancement of lung response to Saccharopolyspora rectivirgula*, Am J Respir Crit Care Med 149(2 Pt1):490-494.

Gudmundsson, G and Hunninghake G.W., 1997, *Interferon-gamma is necessary for the expression of hypersensitivity pneumonitis*, J Clin Invest 99(10):2386-2390.

Denis, M. et al., 1993, *A Study of monokine release and natural killer activity in the bronchoalveolar lavage of subjects with farmer's lung*, Am Rev Respir Dis 147(4): 934-939.

Wahlstrom, J. K. et al., 2001, *Analysis of intracellular cycokines in CD4(+) and CD8(+) lung and blood T cells in sarcoidosis*, Am J Respir Crit Care Med 163(1): 115-121.

Cohn, L. et al., 2001, *IL-4 promotes airway eosinophilia by suppressiong IFN-gamma production: definnin a novel role for IFN-gamma in the regulation of allergic airway inflammation*, J Immunol 166(4):2760-2767.

Laliberte, R. et al., 2001, *Decreased capacity of asthmatic bronchial fibroblasts to degrade collagen*, Matrix Biol Jan 19(8): 743-753.

Boulet, L. P. et al., 2000, *Airway hyperresponsiveness, inflammation, and subepithelial collagen deposition in recently diagnosed versus long-standing mild asthma. Influence of inhalend corticosteroids*, Am J Respir Crit Care Med 162 (4 Pt 1):1308-1313.

Dempsey, O. J. 2000, *Leukotriene receptor antagonist therapy*, Postgrad Med J 76(902): 767-773.

Busse, W. W., 1998, *Leukotrienes and inflammation*, Am J Respir Crit Care Med 157 (6Pt) 2: S210-213; discussion S247-248.

Zisman, D. A. et al., 2000, *Cyclophosphamide in the treatment of idiopathic pulmonary fibrosis: a prospective study in patients who failed to respond to corticosteroids*, Chest 117(6): 1619-1626.

Redington, A. E., 2000, *Fibrosis and airway remodeling*, Clin Exp Allergy 30 Suppl 1: 42-45.

Frew, A. J. and Plummeridge, M. J., 2001, *Alternative agents in asthma*, J Allergy Clin Immunol 108(1): 3-10.

Thompson D.C. et al., *Nicotinic agonist modulation of feline bronchomotor tone*, Clinical and experimental pharmacology and physiology, vol. 17, No. 2, 1990, pp. 83-97.

Feldbaek et al., 2000, Novel Potent Ligands for the Central Nicotinic Acetylcholine Receptor: Synthesis, Receptor Binding and 3D-QSAR Analysis, J. Med. Chem. 43, 2217-2226.

Romanelli et al., 2001, Structure-Affinity Relationships of a Unique Nicotinic Ligand: N1-Dimethyl-N4-phenylpiperazinium Iodide (DMPP), J. Med. Chem. 44, 3946-3955.

Toma et al., 2002, 6-Chloropyridazin-3-yl Derivatives Active as Nicotinic Agents: Synthesis, Binding and Modeling Studies, J. Med. Chem. 45, 4011-4017.

Manetti et al., 1999, Hybridized and Isosteric Analogues of N1-Acetyl-N4-dimethyl-piperazinium Iodide (ADMP) and N1-Phenyl-N4-dimethyl-piperazinium Iodide (DMPP) with Central Nicotinic Action, Bioorganic & Medicinal Chemistry 7, 457-465.

Guandalini et al., 2005, Rigid analogs of DMPP as probes for the nicotinic receptors, IL Farmaco 60, 99-104.

Hanson R.N. 1983, Preparation and Evaluation of Radioiodinated Phenylpiperazines as Adrenomedullary Imaging Agents, Int. J. Nucl. Med. & Biol. 10(4): 219-222.

Zilber, A.P., *Respiratory Failure*, Moscow "Meditsina", 1989, pp. 288-289 and 295-296.

Berkow, R., Guide to Medicine, vol. 1, Moscow, "MIR", 1997, pp. 450-451.

Reynold A. Panettieri, Jr., Chronic Obstructive Lung Disease, Pathophysiology of Lungs, Moscow, "Binom", 2001, pp. 95-98.

Beleslin et al., *Central Nicotinic Receptors: Vomiting, Ear Twitching and Panting*, Brain Res. Bull., vol. 11, No. 3, pp. 299-302.

Fernandez, E., et al., Journal of Neurochemistry, 1999, vol. 73, No. 1, pp. 169-178.

Flenley, D.C., *New drugs in respiratory disorders: I.*, Br. Med. J. (Clin. Res. Ed.), 1983, Mar. 12; 286(6368): 871-875.

Becker, A.B. et al., *The bronchodilator effects and pharmacokinetics of caffeine in asthma*, N. Engl. J. Med., 1984 Mar. 22; 310(12); 743-6.

Baldassarre, Sandra et al., *Asthma attacks induced by low doses of celecoxib, aspirin and acetaminophen.*, J. Allergy and Clin. Immunol. 2006, 117(1):215-217.

Etter, J.-F., *Cytisine for Smoking Cessation*: A Literature Review and a Meta-analysis. Arch. Intern. Med., Aug. 14-28, 2006; 166(15): 1553-9.

Wang et al., *Interferon gamma Induction of Pulmonary Emphysema in the Adult Murine Lung*, J. of Experimental Medicine, vol. 192, No. 11, Dec. 4, 2000, pp. 1587-1599 (XP-002257504).

Database WPI Derwent publication Ltd. London, GB; An 2000-291290 antiasthmatic drug as tablet and a method of tablet preparation & RU 2 127 123 A. (Moscchem-Pharm Prodm Assoc) Mar. 10, 1999.

\* cited by examiner

Example 1

* = p < 0.05 compared to SR group

Example 2

Example 3

Example 4

\* = p < 0.05 ; n = 4

Example 5

Example 6

\* = p < 0.005

\* = p < 0.005

$* = p < 0.05$

Example 7

Example 8

Example 9

NICOTINIC RECEPTOR AGONISTS FOR THE TREATMENT OF INFLAMMATORY DISEASES

FIELD OF THE INVENTION

The present invention relates to the treatment of inflammatory diseases, including a variety of pulmonary diseases, through the use or administration of nicotinic receptor agonists.

BACKGROUND OF THE INVENTION

Although we breathe more than one cubic meter of air every hour, our lung defense mechanisms usually deal with the large quantities of particles, antigens, infectious agents and toxic gases and fumes that are present in inhaled air. The interaction of these particles with the immune system and other lung defense mechanisms results in the generation of a controlled inflammatory response which is usually protective and beneficial. In general, this process regulates itself in order to preserve the integrity of the airway and alveolar epithelial surfaces where gas exchange occurs. In some cases, however, the inflammatory response cannot be regulated and the potential for tissue injury is increased. Depending on the type of environmental exposure, genetic predisposition, and a variety of ill-defined factors, abnormally large numbers of inflammatory cells can be recruited at different sites of the respiratory system, resulting in illness or disease.

The inflammatory response to inhaled or intrinsic stimuli is characterized by a non-specific increase in the vascular permeability, the release of inflammatory and chemotactic mediators including histamine, eicosanoids, prostaglandins, cytokines and chemokines. These mediators modulate the expression and engagement of leukocyte-endothelium cell adhesion molecules allowing the recruitment of inflammatory cells present in blood.

A more specific inflammatory reaction involves the recognition and the mounting of an exacerbated, specific immune response to inhaled antigens. This reaction is involved in the development of asthma, Hypersensitivity pneumonitis (HP) and possibly sarcoidosis. Dysregulation in the repair mechanisms following lung injury may contribute to fibrosis and loss of function in asthma, pulmonary fibrosis, chronic obstructive pulmonary disease (COPD), and chronic HP.

It was previously reported that the incidence of HP is much lower among current smokers than in non-smokers (1-4). Sarcoidosis is also less frequent in smokers than in non smokers (5, 6). The mechanisms underlying the beneficial effects of cigarette smoking on the development of HP and other inflammatory diseases are still unknown but may be linked to the immunomodulatory effect of nicotine. There are clinical observations of asthma de novo or exacerbation after smoking cessation. Proof of this is difficult to obtain and any protective effects of nicotine in the prevention or treatment of asthma are likely overwhelmed by the negative effects of tobacco smoke with its thousands of constituents.

The protective effect of smoking has also been reported in other diseases, the most studied being ulcerative colitis, an inflammatory intestinal disease (7, 8). Nicotine has been successfully used in the treatment of this disease (9, 10). Other studies have looked at the possible therapeutic value of nicotine in the treatment of Alzheimer's disease and Parkinson's disease (11, 12).

Nicotinic receptors are pentamers made up of five polypeptide subunits which act as ligand-gated ions channels. When the ligand binds to the receptor, a conformational change in the polypeptide occurs, opening a central channel that allows sodium ion to move from the extracellular fluid into the cytoplasm. Four types of subunits have been identified: $\alpha$, $\beta$, $\gamma$ and $\delta$. The receptor can consist of any combination of these four types of subunits (13). Recent work has shown that alveolar macrophages (AM) can express the $\alpha$-7 subunit (14), while bronchial epithelial cells express the $\alpha$-3, $\alpha$-5 and $\alpha$-7 subunits (15), and lymphocytes the $\alpha$-2, $\alpha$-5, $\alpha$-7, $\beta$-2 and $\beta$-4 subunits (14). Fibroblasts (16) and airway smooth muscles cells (17) also express these receptors. Therefore, resident pulmonary cells (AM, dendritic cells, epithelial cells, fibroblasts, etc.) and those recruited in inflammatory diseases (lymphocytes, polymorphonuclear cells) express nicotinic receptors.

Nicotinic receptor activation in lymphocytes affects the intracellular signalization, leading to incomplete activation of the cell. In fact, nicotine treatment upregulates protein kinase activity, which in turn upregulates phospholipase A2 (PLA2) activity. PLA2 is responsible for cleaving phosphoinositol-2-phosphate (PIP2) into inositol-3-phosphate (IP3) and diacylglycerol (DAG) (18, 19). The continuous presence of IP3 in the cell would appear to result in the desensitization of calcium stores, leading to their depletion (19). This observation could explain the fact that nicotine-treated lymphocytes do not release enough calcium into the cytoplasm to activate transcription factors such as NFk-B (20).

Nicotine, the major pharmacological component of cigarette smoke, is one of the best known nicotinic receptor agonists (21). This natural substance has well defined anti-inflammatory and immunosuppressive properties (22), and may have anti-fibrotic properties (23). Exposure of animals to smoke from cigarettes with high levels of nicotine is more immunosuppressive than that from low-nicotine cigarettes (24). Moreover, treatment of rats with nicotine inhibits the specific antibody response to antigens and induces T cell anergy (25). Although they are increased in number, AM from smokers show a decreased ability to secrete inflammatory cytokines in response to endotoxins ((20, 25, 26)) and nicotine seems to be the responsible component of this inhibition (26). One study also showed that peripheral blood lymphocytes from smokers express higher levels of FAS ligand (FASL) and that nicotine increases FASL expression on lymphocytes from non-smokers, indicating that nicotine may affect cell apoptosis (27). Nicotine was also shown to have an inhibitory effect on the proliferation and extracellular matrix production of human gingival fibroblasts in vitro (23). Of interest, nicotine treatment seems to up-regulate the expression of nicotinic receptors (28).

Nicotinic agonists may down-regulate T cell activation, indeed, nicotine has been shown to affect T cell expression of the co-stimulatory molecules CD28 and CTLA4 (29).

The B7/CD28/CTLA4 co-stimulatory pathway plays a key regulatory role in T-cell activation and homeostasis (30, 31). Two signaling pathways are involved. A positive signal involves the engagement of B7 (CD80/CD86) molecules with T cell CD28 receptors which results in the potentiation of T cell responses (proliferation, activation, cytokine expression, and survival) (32). A negative signal involves B7 interactions with CTLA4 on activated T cells, leading to a downmodulation of T cell responses (33, 34). The balance between CD28 and CTLA4 derived signals may alter the outcome of T-cell activation.

In HP, it was previously reported that an upregulation of B7 molecule expression on AM in patients with active HP (35) and in murine HP (36). It was also shown that a blockade of the B7-CD28 co-stimulatory pathway in mice inhibited lung inflammation (36). These results also demonstrated that the expression of B7 molecules on AM is lower in smokers than in non-smokers and that an in vitro influenza virus infection is able to upregulate B7 expression in normal human AM but not in AM from smokers; whether this is due to nicotine or other substances present in cigarette smoke is unknown (35). An up-regulation of the B7 molecules has also been reported in asthma (37, 38) and sarcoidosis (39).

Epibatidine is the most potent nicotinic agonist known so far (40). It has anti-inflammatory and analgesic properties. In fact, its analgesic potential is two hundred times that of morphine (40). This molecule is also known to inhibit lymphocyte proliferation in vitro (41). The binding of epibatidine to the receptor is non-specific (42). Unfortunately, epibatidine has major toxic side effects mostly on the cardiovascular and the central nervous systems making it inappropriate for use as an anti-inflammatory drug to treat pulmonary diseases (40).

Dimethylphenylpiperazinium (DMPP) is a synthetic nicotinic agonist that is non-specific (13). Its potency for the receptor is about the same as nicotine, depending on the kind of cells implicated in the stimulation (43). Its advantage over nicotine and other nicotinic agonists is that its chemical configuration prevents it from crossing the blood-brain barrier, thus causing no addiction or other central nervous effects (13). The anti-inflammatory properties of DMPP are not well described. However, it has been shown that a chronic in vivo treatment could decrease the number of white blood cells, decrease the cytokine production by splenocytes and decrease the activity of natural killer cells (44). The effect of DMPP on airway smooth muscle cells has also been tested. DMPP has an initial short contractive effect which is followed by a relaxing effect when the cells are in contact with the agonist for a longer period of time (45). This bronchodilatory effect would not in itself make DMPP a potentially useful treatment of asthma, since more potent bronchodilators are currently available on the market (B2 agonists). However, the properties of this nicotinic receptor agonist are important since this drug could be safely administered to asthmatics and COPD patients for its anti-inflammatories properties. Moreover, there is no evidence that DMPP has any toxic effect on major organs such as the heart, the brain, the liver or the lungs.

Despite advances in the treatment of inflammatory illnesses, including pulmonary inflammatory diseases, treatment using available drugs or agents frequently results in undesirable side effects. For example, the inflammation of COPD is apparently resistant to corticosteroids, and consequently the need for the development of new anti-inflammatory drugs to treat this condition has been recognized (46).

Similarly, while corticosteroids and other immunosuppressive medications have been routinely employed to treat pulmonary fibrosis, they have demonstrated only marginal efficacy (47).

There is thus a need for new and reliable methods of treating inflammatory diseases, including pulmonary inflammatory diseases, in a manner that alleviates their symptoms without causing side effects.

SUMMARY OF THE INVENTION

In accordance with the present invention, there is provided a novel method for treating inflammatory diseases. Specifically, a novel method is described for treating pulmonary inflammatory diseases through the use or administration of nicotinic receptor agonists.

The idea of using nicotine or other nicotinic receptor agonists to treat inflammatory pulmonary disease is novel. Despite the impressive anti-inflammatory and immunosuppressive properties of nicotine and other nicotinic receptor agonists, their usefulness in the treatment of allergic and other inflammatory lung diseases has not previously been disclosed. Nicotine itself is a safe substance that does not seem to have any long term side effects (48,49). Smoke-related diseases of the lungs, heart and arteries are not caused by nicotine but by the thousands of other chemicals present in the inhaled smoke. The main problem is that nicotine crosses the blood-brain barrier, inducing addiction. These are major reasons for the lack of prior interest in nicotinic agonists in the treatment of lung diseases. The harmful effects of cigarette smoking are obvious. Although nicotine is not responsible for the toxic effects of cigarette smoking (49), the association remains.

The present invention thus proposes the use nicotinic receptor agonists, such as DMPP, to treat inflammatory lung diseases such as asthma, COPD, interstitial pulmonary fibrosis (IPF), sarcoidosis, HP, and bronchiolitis obliterans with organizing pneumonitis (BOOP). The drug could be administered orally, or preferably by targeted delivery directly to the lung by aerosolisation with different and preferred vehicles thus minimizing any systemic effects.

The anti-inflammatory and immunosuppressive properties, as well as minimal side effects, of nicotinic receptor agonists make these drugs ideally suited for medical use in the treatment of a large variety of lung diseases that are characterized by bronchial or interstitial inflammation. These diseases include diseases such as asthma, COPD, IPF, sarcoidosis, HP and BOOP.

Other objects, advantages and features of the present invention will become more apparent upon reading the following non-restrictive description of preferred embodiments thereof, given by way of example only with reference to the accompanying drawings.

DESCRIPTION OF THE PREFERRED EMBODIMENTS

Figure 1:
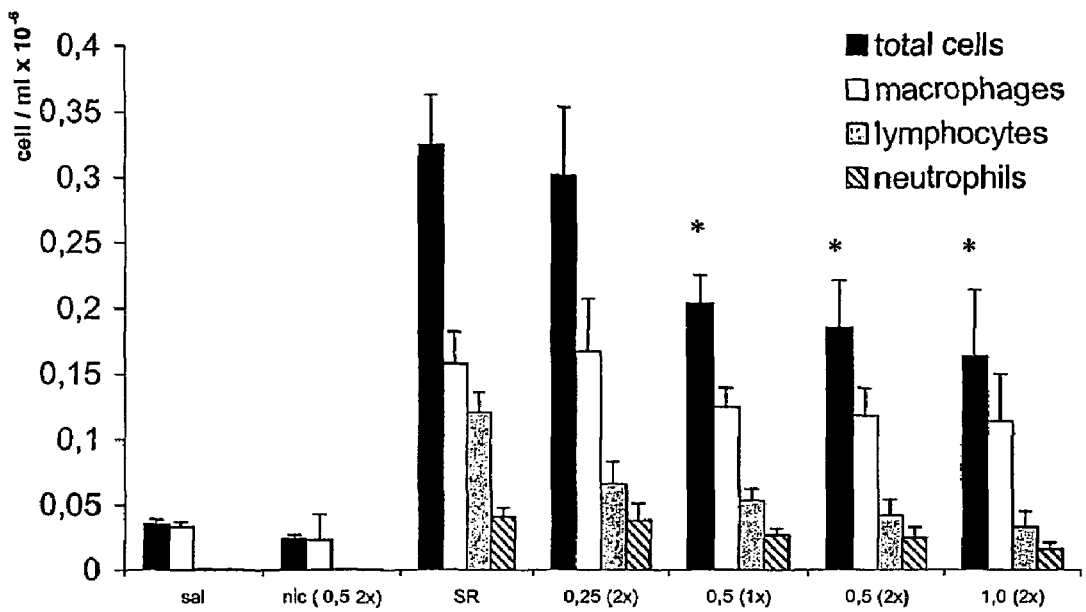
FIG. 1: Total and differential cell counts in BAL cells. There was a marked inhibition of total cell counts in nicotine treated mice due mainly to a decrease in the lymphocyte population.

The presence of nicotinic receptors on inflammatory and pulmonary cells has been described previously. However, the novelty of the present invention resides in the observation that nicotinic receptor agonists appear to be useful in the treatment of inflammatory lung diseases, and in the related discovery of the anti-inflammatory and immunosuppressive properties of nicotinic agonists specifically directed against mechanisms involved in the pathogenesis of such inflammatory pulmonary diseases as asthma, HP, sarcoidosis, BOOP, IPF, and COPD. An example of this is the effect of cigarette smoke on the expression of the B7 co-stimulatory molecules.

Two animal models were used to study the effects of nicotinic antagonists in inflammatory pulmonary diseases: an HP model and an asthma model. With both of these models, the effects of nicotinic receptor agonists (both selective and non-selective) were studied on lung physiology, and inflammation. In vitro studies were performed using isolated inflammatory cells from the animal studies or from patients as well as commercially available cell lines in an attempt to understand the mechanisms by which nicotinic agonists down-regulate inflammation.

Initially, experiments were conducted with non-specific agonists, i.e agonists that bind to all nicotinic receptor subunits (nicotine, dimethylphenylpiperazinium (DMPP) and epibatidine) (13, 42). A β4 subunit specific agonist, cytisine (42), was also tested to see whether a specific stimulation could also have anti-inflammatory effects.

For the purposes of the present application, the term "animal" is meant to signify human beings, primates, domestic animals (such as horses, cows, pigs, goats, sheep, cats, dogs, guinea pigs, mice, etc.) and other mammals. Generally, this term is used to indicate living creatures having highly developed vascular systems.

For the purposes of the present invention, agonists or agents are molecules or compounds that bind to and modulate the function of the nicotinic receptor. Preferred agents are receptor-specific and do not cross the blood-brain barrier, such as DMPP. Useful agents may be found within numerous chemical classes, though typically they are organic compounds and preferably, small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways as described above, e.g. to enhance their proteolytic stability. Other methods of stabilization may include encapsulation, for example, in liposomes, etc. The subject binding agents are prepared in any convenient way known to those skilled in the art.

For therapeutic uses, agents affecting nicotinic receptor function may be administered by any convenient means. Small organics are preferably administered orally; other compositions and agents are preferably administered parenterally, conveniently in a pharmaceutically or physiologically acceptable carrier, e.g., phosphate buffered saline, or the like. Typically, the compositions are added to a retained physiological fluid such as blood or synovial fluid.

As examples, many such therapeutics are amenable to direct injection or infusion, topical, intratracheal/nasal administration e.g. through aerosol, intraocularly, or within/on implants (such as collagen, osmotic pumps, grafts comprising appropriately transformed cells, etc. with therapeutic peptides. Generally, the amount administered will be empirically determined, typically in the range of about 10 to 1000 μg/kg of the recipient. For peptide agents, the concentration will generally be in the range of about 50 to 500 μg/ml in the dose administered. Other additives may be included, such as stabilizers, bactericides, etc. These additives will be present in conventional amounts.

Nicotinic agonists would not replace all drugs that are currently used to treat inflammatory lung diseases and the airflow obstruction that is often associated with these diseases. Bronchodilators remain useful for the immediate release of bronchospasms. However, bronchodilators have no effect on the underlying cause or inflammation.

Corticosteroids are potent anti-inflammatory drugs. Their systemic use causes major side effects that preclude their long-term uses whenever possible. Inhaled poorly absorbed steroids are useful to treat airway inflammation. At low doses these drugs have little or no side effects. However, higher doses increase the risks for oral candidasis, vocal cords paralysis, cataracts and osteoporosis. Inhaled steroids have no effects on lung interstitium and have no anti-fibrotic properties (57).

More recent drugs, such as anti-leukotrienes, are useful in some asthmatics (58) but have no effects in COPD and other lung diseases. These drugs have anti-inflammatory properties limited to the components of inflammation caused by leukotrienes (59). The treatment of interstitial lung disease such as IPF, Sarcoidosis, HP, and BOOP basically rests on the use of systemic corticosteroids. This treatment is effective in controlling some of the inflammation but unfortunately induces serious side effects and does not reverse underlying fibrotic changes. Immunosuppressive agents such as cyclophosphamide and azathioprine are sometimes tried in severe IPF but their therapeutic values are unproven and at most, very limited (60). In essence, lung fibrosis is usually progressive and untreatable, with most IPF patients dying of this condition (61).

Nicotinic agonists may be useful as a steroid sparing or replacing drug. By targeting their delivery to the lung phagocytes, these drugs could be helpful in controlling both airway and interstitial inflammation. One major advantage of nicotinic agonists over corticosteroids, besides having fewer side effects, is the fact that these agonists have a direct effect on fibroblasts and could therefore prevent or reverse fibrosis in the airways and in the lungs, something corticosteroids cannot do. Interstitial fibrosis is the hallmark if IPF, a major sequel of HP and sarcoidosis, and airway fibrosis is a prevailing finding in chronic asthma (57).

Other substances are actively being studies as potential new treatments for inflammatory lung diseases. Many cytokines are specifically targeted (e.g. IL-5, IL-13, IL-16 . . . ) (62). It is believed that because of the complexity of pathways involved in inflammation, any one specific cytokine or other inflammatory mediator is unlikely to have a significant impact on the treatment of these lung diseases. Nicotinic receptor agonists, not unlike corticosteroids, have the advantage of targeting a broad spectrum of the inflammatory response. Therein lies their potential in the treatment of inflammatory lung diseases.

EXAMPLES

I—Hypersensitivity-like Inflammation

Effect of nicotinic agonists on long term-nnduced hypersensitivity pneumonitis (HP) in Mice.

Example 1

In Vivo HP Studies

The hypothesis is that the stimulation of nicotinic receptors with nicotine down-regulates the immune response to HP antigens via inflammatory cytokine suppression and inhibition of specific antigen-mediated cellular activation.

Figure 2:
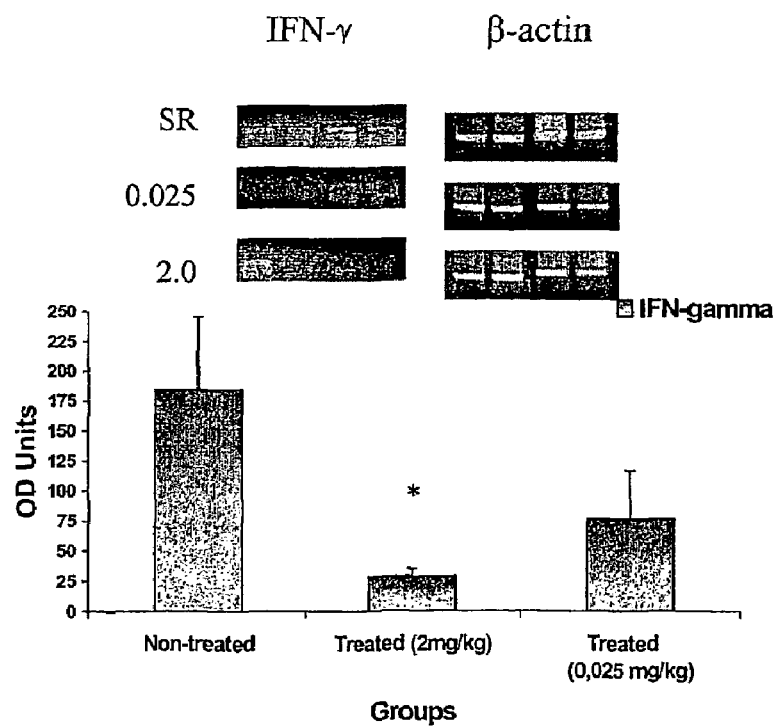
FIG. 2: IFN-γ mRNA expression in isolated lung mononuclear cells. A significant inhibition of IFN-γ mRNA was observed.

This model was selected because, as mentioned previously, the incidence of HP is lower in smokers than in non-smokers (50), and because this model is well described. HP was induced by the administration of *Saccharopolyspora rectivirgula* (SR) antigen, the causative agent of farmer's lung (51), a form of HP. Mice were simultaneously treated with intraperitoneal (IP) nicotine, with doses ranging from 0.5 to 2.0 mg/kg, twice a day. Nicotine administration significantly reduced the number of total cells found in the bronchoalveolar lavage (BAL) of these mice. The population that was the most affected by nicotine treatment were lymphocytes (FIG. 1). Pulmonary macrophages and lymphocytes were isolated, and stimulated with anti-CD3+recombinant IL-2. The production of IFN-γ mRNA by these cells, a cytokine known to be involved in the development of HP and other pulmonary inflammatory diseases (52), was measured. Cells from nicotine treated animals showed significantly lower expression of IFN-γ mRNA than cells from non-treated animals (FIG. 2).

Example 2

In Vitro Studies Showing the Effect of Nicotinic Agonists on Cytokine Expression To further clarify the mechanisms involved in suppressive effect of nicotine in the in vivo model, an alveolar macrophage cell line was used.

Figure 3:
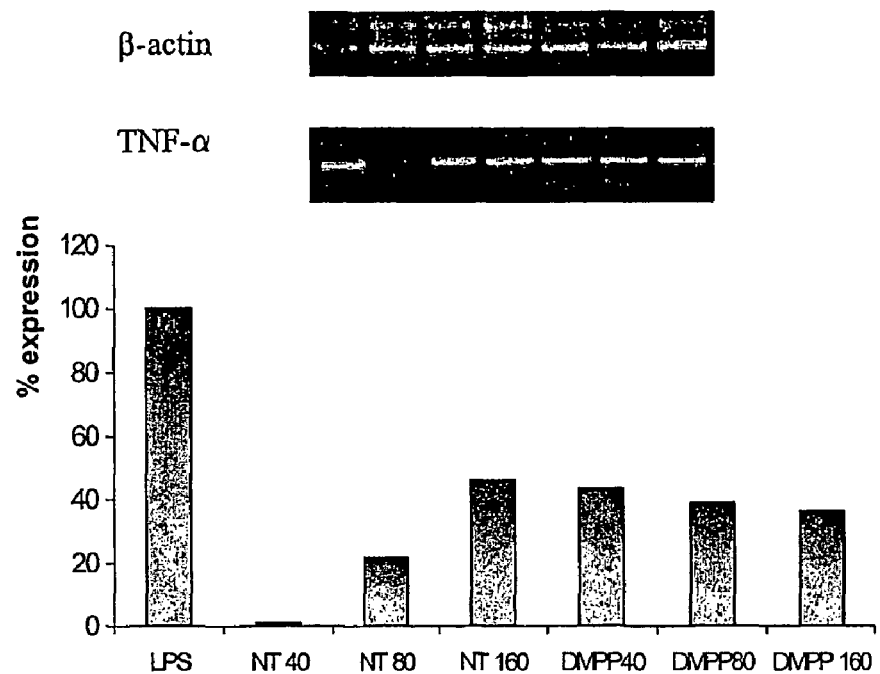
FIG. 3: TNF-a mRNA expression was induced by a 24 h Lipopolysaccharides component of gram negative cell walls (LPS) stimulation. Results are expressed as a % of expression, 100% being attributed to the LPS alone group. The intensity of the band was obtained by dividing the intensity of the TNF-α band by that of β-actin. Treatment of stimulated cells with different doses (40 to 160 uM for nicotine and DMPP) induced a drop of TNF-α mRNA expression. The greatest effect was obtained with the 40 uM concentration of nicotine (a 98% reduction of expression), while all doses of DMPP caused a 60 to 50% reduction of expression.
Figure 4:
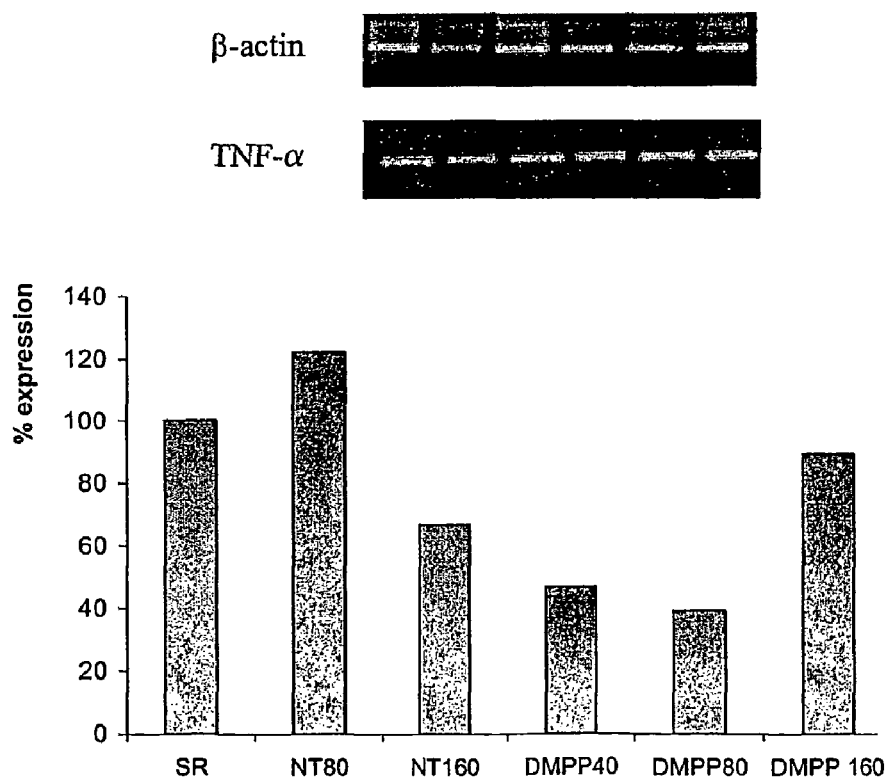
FIG. 4: TNF-α mRNA expression was induced by a 24 h saccharopolyspora rectivirgula (SR) stimulation. Results are expressed as described in FIG. 5. Treatment of stimulated cells with different doses (80 and 160 μM for nicotine and 40 to 160 μM for DMPP) induced a down-regulation of TNF-α mRNA expression. Only the 160 μM dose of nicotine had an effect on mRNA expression, while the 40 and 80 μM doses of DMPP induced up to 60% of reduction of TNF-α mRNA expression.
Figure 5:
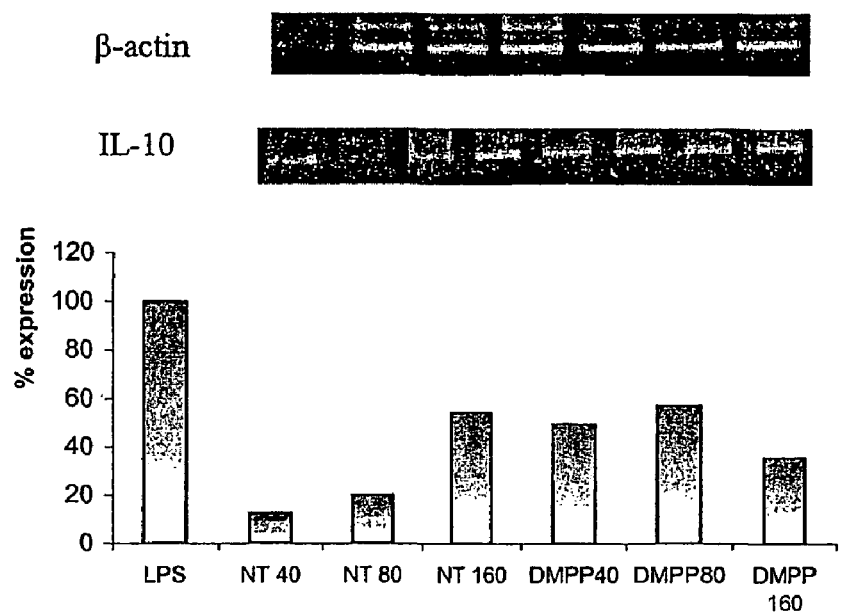
FIG. 5: IL-10 mRNA expression was induced by a 24 h LPS stimulation. Results are expressed as described in FIG. 3. Treatment of stimulated cells with different doses (40 to 160 μM for both nicotine and DMPP) induced a down-regulation of IL-10 mRNA expression. The largest drop of expression (a 87% reduction) occurred with 40 uM nicotine. DMPP induced a 55 to 40% reduction of expression for all three doses.
Figure 6:
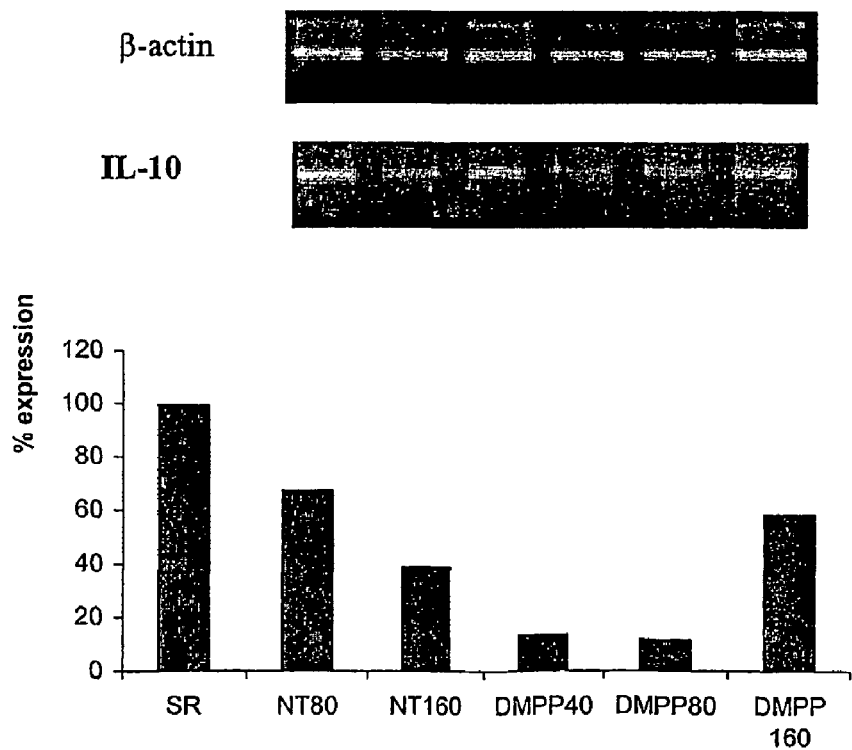
FIG. 6: IL-10 mRNA expression was induced by a 24 h SR stimulation. Treatment of stimulated cells with different doses (80 and 160 µM for nicotine and 40 to 80 µM for DMPP) induced a down-regulation of IL-10 mRNA expression. The greatest drop in mRNA expression with the nicotine treatment occurred at 160 µM (60% drop of expression), and at 80 µM (90% drop of expression) with the DMPP treatment.

The effect of nicotine or DMPP treatment on AMJ2-C11 cells was tested on TNF-α and IL-10 mRNA expression by RT-PCR. These cytokines are involved in the development of pulmonary inflammatory diseases such as HP, asthma and sarcoidosis (52-55). Nicotine and DMPP treatments showed a great decrease in TNF mRNA expression (up to a 98% reduction of expression in Lipopolysaccharides component of gram negative cell walls (LPS) stimulated and treated with 40 μM nicotine), but not in a dose-dependant manner (FIG. 3). Similar results were observed with SR-stimulated cells (FIG. 4). This non-dose dependant response can be explained by nicotinic receptor desensitization due to a large quantity of agonist in the medium. IL-10 mRNA expression was also impaired by nicotine and DMPP treatment. The best down-regulation occurred at a dosage of 40 μM nicotine (LPS stimulated; 88 % reduction of mRNA expression; FIG. 5) and at a dosage of 80 μM DMPP (SR stimulated ; 87% mRNA expression reduction; FIG. 6). Once again, the effect was not dose-dependant.

Figure 7:
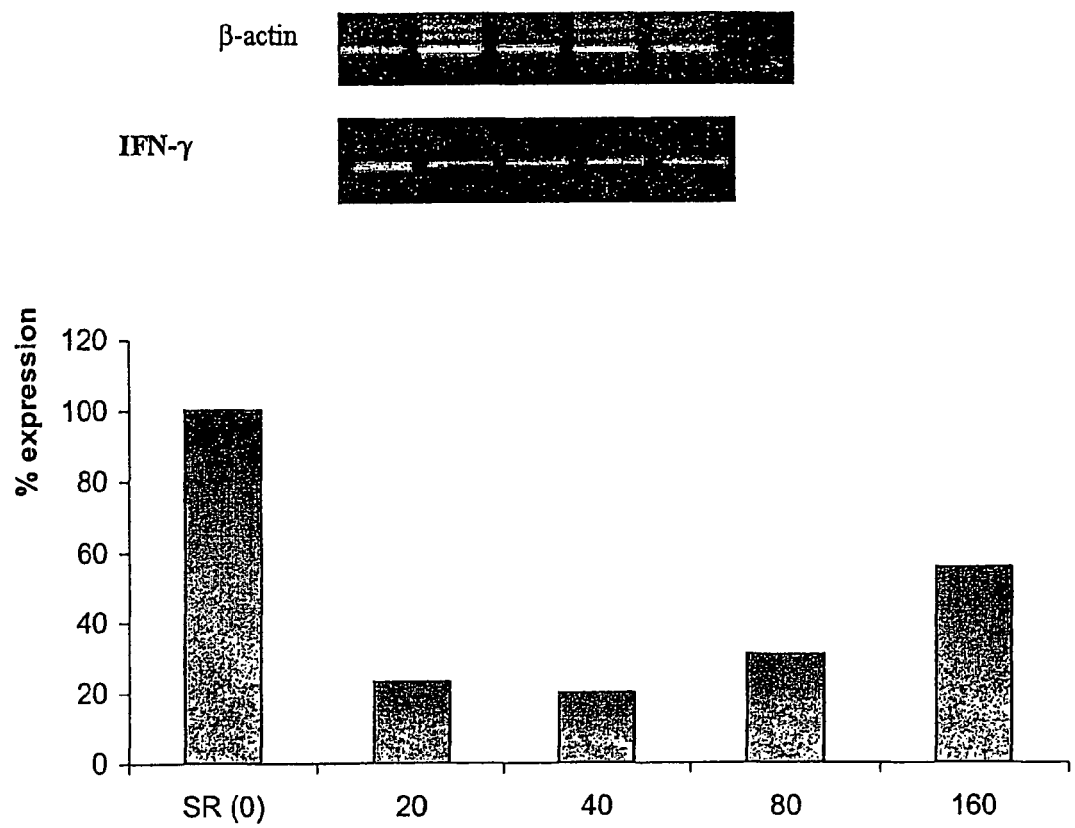
FIG. 7: IFN-γ mRNA expression was induced in RAW 264.7 cells by a 24 h LPS stimulation. Results are expressed as described in FIG. 3. Treatment of stimulated cells with different doses of DMPP induced a reduction in IFN-γ mRNA expression. The largest drop of expression (a 80% reduction) occurred with 40 µM DMPP.

Another macrophage cell line (RAW 264.7, ATCC) was used to test the effect of DMPP on IFN-γ expression by RT-PCR, because AMJ2-C11 cells did not appear to express IFN-γ mRNA (data not shown). Cells were stimulated with 50 μg/ml of SR antigen and incubated with DMPP at doses ranging from 40 to 160 μM. DMPP treatment reduced the expression of INF-γ in these cells by up to 75% with the 40 μM dose (FIG. 7). Once more, the effect did not seem to be dose-dependant.

Example 3

In Vitro Effects of Nicotinic Agonists on Co-stimulatory Molecule Expression

Figure 8A:
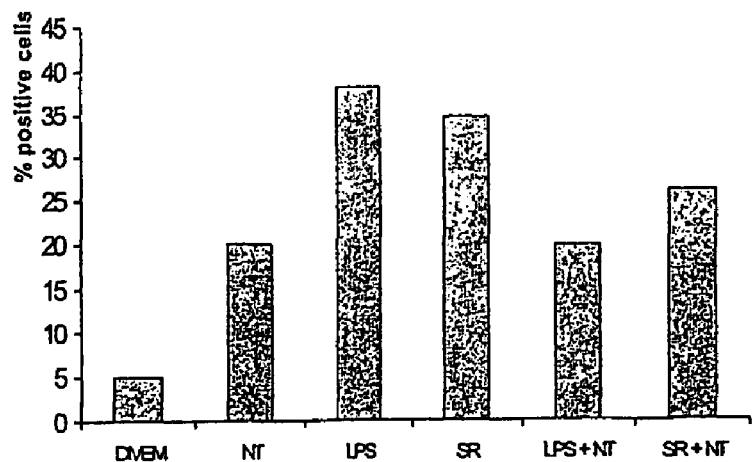
FIG. 8: a) The expression of CD 80 was induced with either LPS (38%) or SR antigen (35%). Nicotine treatment (40 µM for 48 h) reduced the expression to 20% in LPS stimulated cells and 26% in SR stimulated cells. b) The expression of CD 80 was induced with either LPS (38%) or SR antigen (35%). DMPP treatment (40 µM for 48 h) reduced the expression to 17% in LPS stimulated cells and 20% in SR stimulated cells.
Figure 8B:
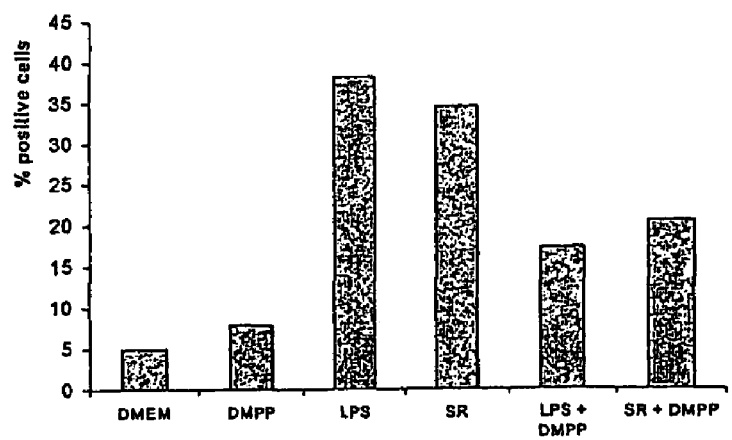

The effects of nicotine and DMPP on B7 (CD80) molecule expression were tested in vitro. AMJ2-C11 cells (mouse alveolar macrophages, from the ATCC) were incubated with 40 μM nicotine or DMPP and stimulated with LPS (0.1 μg/ml) or SR antigen (50 μg/ml) for 48 hours. The percentage of expression of CD80 in treated cells was about one half of the expression found in LPS and SR stimulated non-treated cells (FIGS. 8(a) and (b)).

Example 4

Studies on Human BAL Cells (AM and Lymphocytes)

Figure 9:
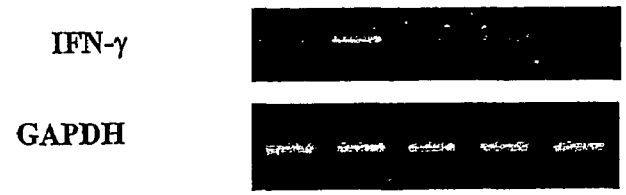
FIG. 9: IFN-γ mRNA expression in T lymphocytes isolated from BAL performed on HP patients. DMPP treatment reduced expression of IFN-γ in these cells.
Figure 9:
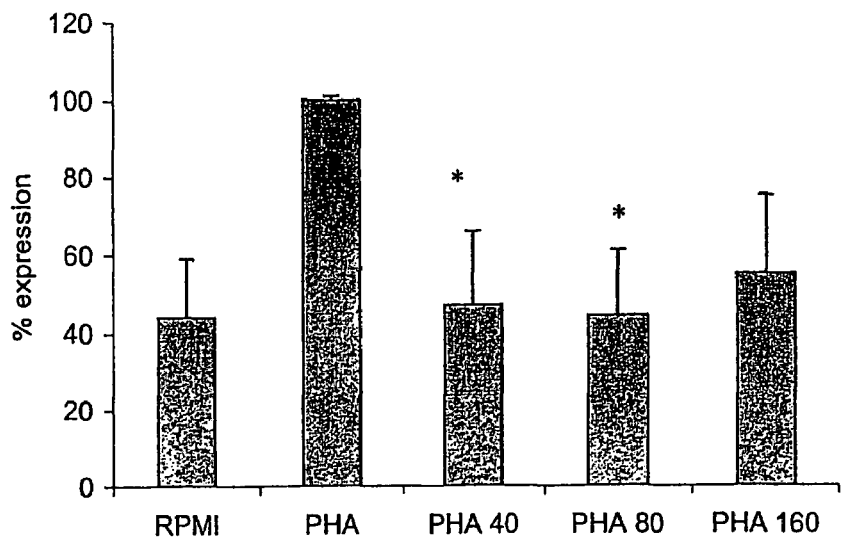

Since one goal was to treat patients with DMPP or similar drugs, the effect of this drug was verified on lymphocytes from patients with HP. BAL were performed on patients with HP. Lymphocytes were isolated from the other BAL cells, stimulated with PHA and incubated with DMPP. The dose-response of DMPP were tested on cytokine mRNA production (by RT-PCR) for IFN-γ (FIG. 9).

Figure 10:
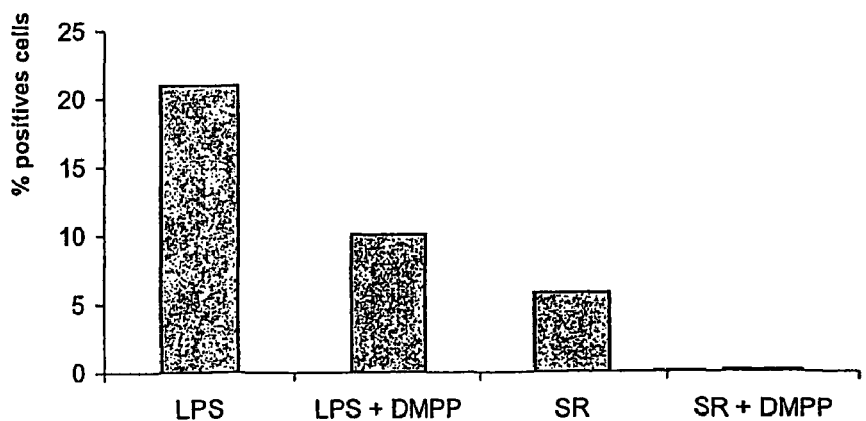
FIG. 10: CD 86 expression in total cells from a BAL that was performed on a normal subject. Cells that were treated with DMPP express 50% less CD 86 than non-treated cells.

A broncho-alveolar lavage was performed on a normal subject, and alveolar macrophages were isolated. SR-stimulated and nicotine or DMPP treated cells showed once again about half of the expression of CD86 than non-treated cells (FIG. 10).

Example 5

Figure 11:
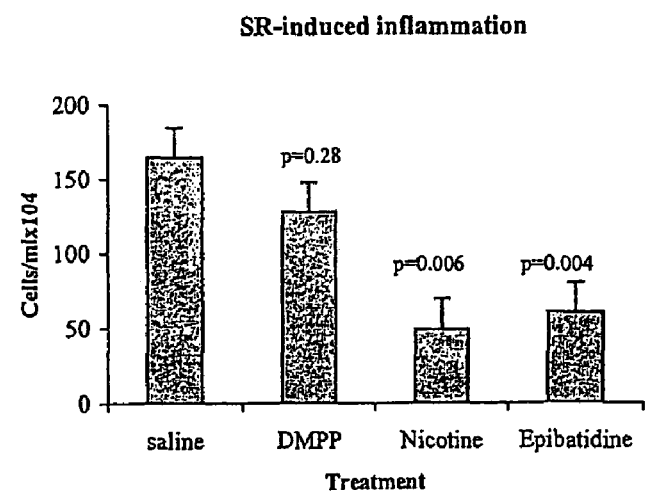
FIG. 11: BAL cells from DMPP, nicotine and epibatidine treated mice. Treatment with nicotine and epibatidine had a significant inhibitory effect on SR-induced inflammation after 24 hours.

Investigation of the Effect of Other Nicotinic Agonists on the Short Term SR-induced Acute Inflammation The intranasal instillation of *Saccharopolyspora rectivirgula* (SR) antigens, the causative agent for farmer's lung, to mice, induces a prominent inflammatory response in the lung. Neutrophils are the first inflammatory cells recruited at the site of inflammation. Treatment of mice with DMPP (0.5 mg/kg), nicotine (0.5 mg/kg) and epibatidine (2 μg/kg) had a marked inhibitory effect on SR-induced inflammation (FIG. 11). Nicotinic agonists were administered intra-nasally in 50 μl volume every 6 h and mice were sacrificed 24 hr after SR instillation.

Figure 12:
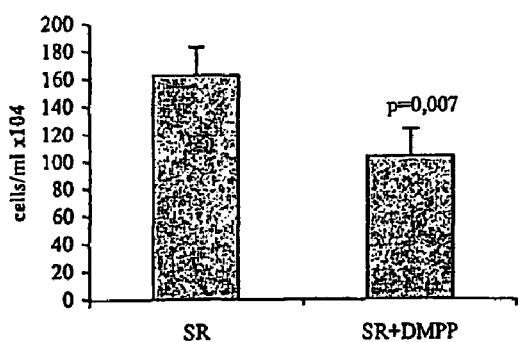
FIG. 12: A significant inhibitory effect of DMPP on lung inflammation was found when we increased the number of animals.

A significant inhibitory effect was observed with nicotine and epibatidine but not with DMPP. However, after increasing the number of mice treated or not treated with DMPP to 15, we did observe a significant inhibition compared to the non-treated group (FIG. 12).

Figure 13:
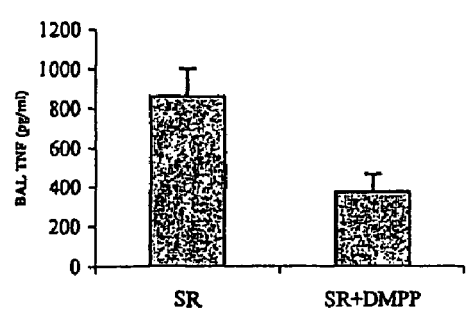
FIG. 13: TNF levels in BAL fluid (BALF) from DMP-treated mice. DMPP decreased significantly BALF TNF levels.
Figure 14:
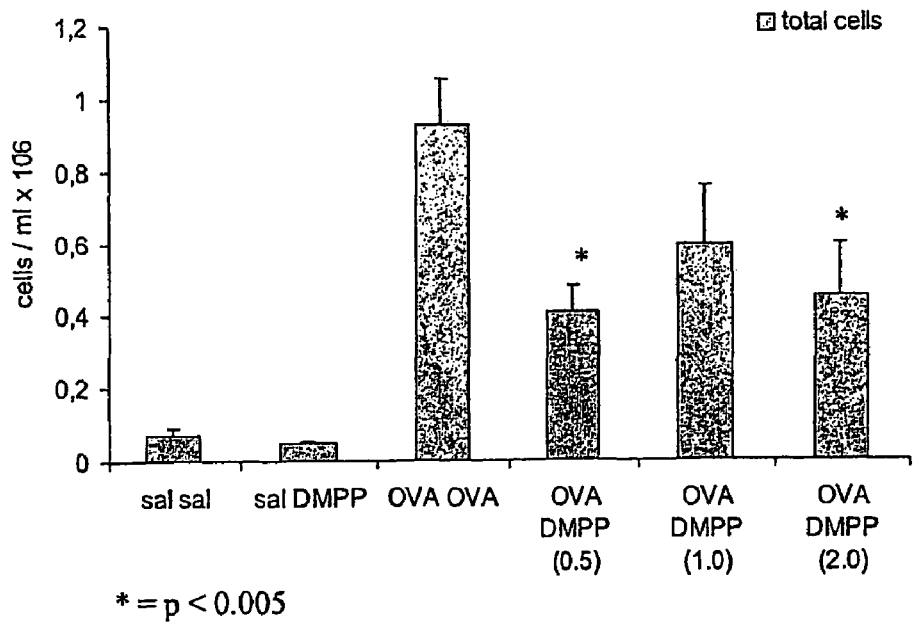
FIG. 14: Effect of intra-peritoneal treatment with increasing doses of DMPP on total cell accumulation in BAL of asthmatic mice. The number of cells was highly elevated in OVA challenged and non-treated mice. The DMPP treatment significantly reduced cell counts at the 0.5 and 2.0 mg/kg doses.
Figure 15:
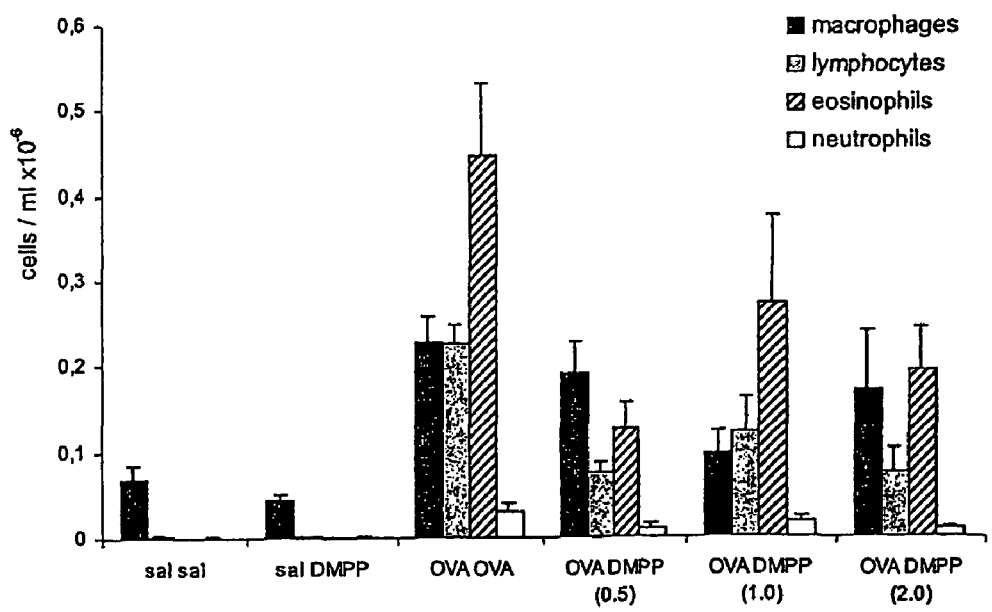
FIG. 15: Differential counts for the dose response. The OVA challenged mice (OVA OVA) had more eoosinophils and lymphocytes in their BAL compared to the control group (sal sal). The DMPP treatment significantly reduced the presence of both osinophils and lymphocytes in BAL in all groups (n=8; p<0.05).
Figure 16:
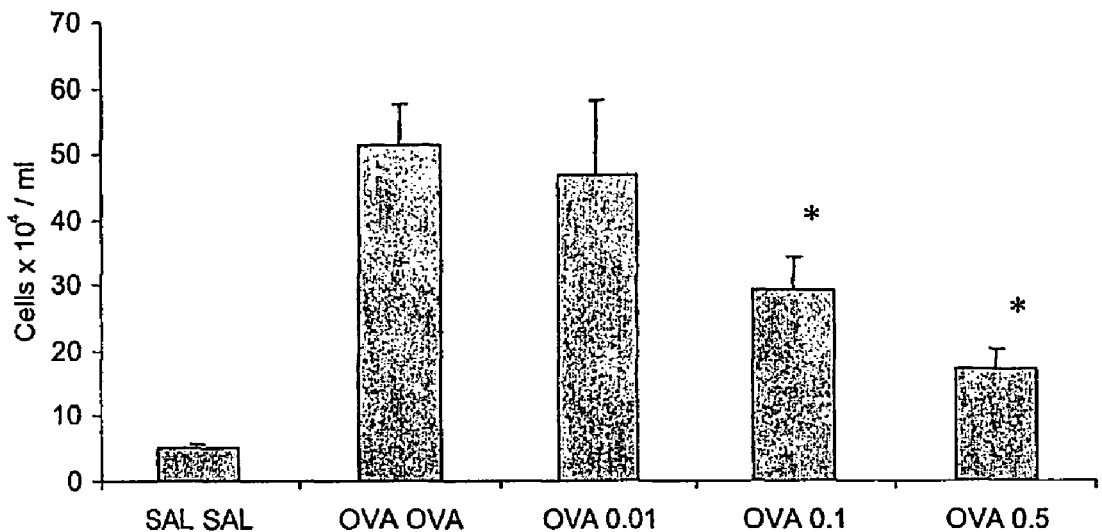
FIG. 16: Second dose response for the DMPP IP treatment effect on total cell accumulation in BAL of asthmatic mice. The number of cells was highly elevated in OVA challenged and non-treated mice. The DMPP treatment significantly reduced total cells at the 0.1 and 0.5 mg/kg doses.
Figure 17:
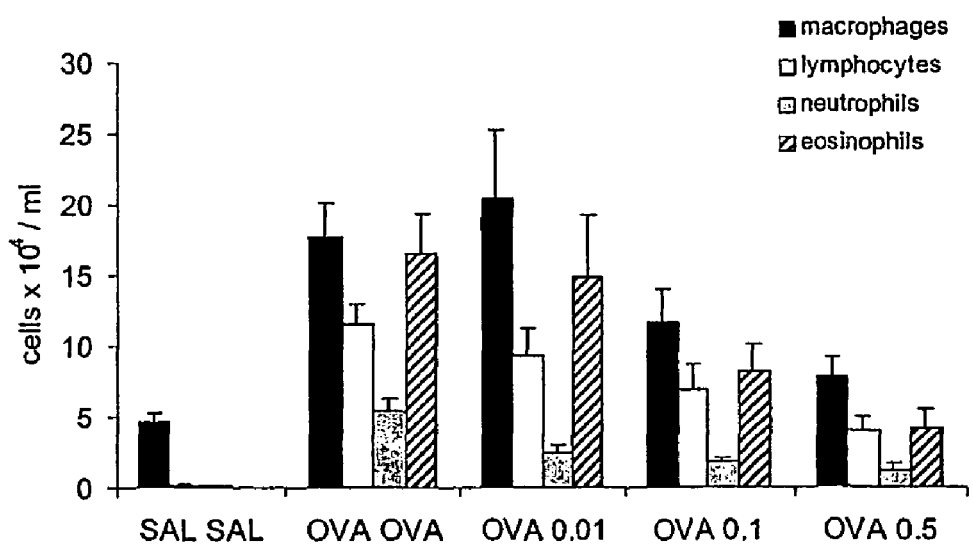
FIG. 17: Differential counts from the second dose response. The DMPP treatment significantly reduced eosinophil and lymphocyte counts in the 0.1 and 0.5 mg/kg doses, 0.5 mg/kg being the most effective dose for the anti-inflammatory effect of DMPP.

Levels of TNF (a pro-inflammatory cytokine) are lower in the broncho-alveolar lavage of DMPP-treated mice (FIG. 13) indicating that the down-regulation of inflammation may result from lower TNF concentrations.

II—Asthma-like Inflammation

Example 6

In Vivo Asthma Model

Similar experiments were performed in ovalbumine-sensitized mice. DMPP allegedly decreases both the inflammatory response and the hyper-responsiveness to inhaled allergens and methacholine.

Groups of Balb/c mice were sensitized by intra-peritoneal injection of 20 μg OVA protein (chicken egg albumin; Sigma-Aldrich) emulsified in 2 mg aluminum hydroxide in PBS. After 4 weeks, challenge doses of 1.5%/50 μl OVA were administered intranasally. The challenge was performed daily for 3 consecutive days and then the mice assessed for allergic inflammation of the lungs 24 h after the last aerosol exposure. Groups of mice were treated with various concentrations of DMPP during the challenge period. Broncho-alveolar lavage (BAL) was performed and the fluid centrifuged at 400 g to separate cells from liquid (FIGS. 14, 15, 16 and 17).

Figure 18:
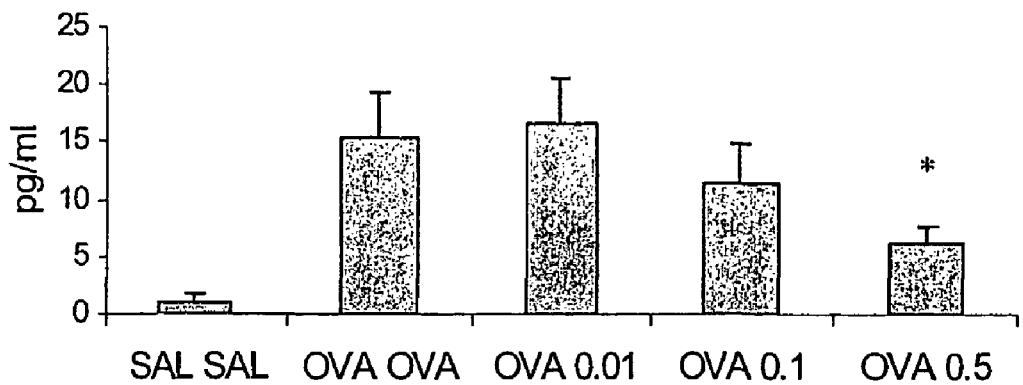
FIG. 18: BAL IL-5 levels from control, asthmatic and treated mice. The OVA challenges increased IL-5 levels in BAL, while the DMPP treatment had a significant inhibitory effect on IL-5 levels in the 0.5 mg/kg treated-group of mice.

The supernatants were used to determine lung IL-5 levels. The total number of BAL cells and differential cell counts were evaluated (FIG. 18).

The experiment was repeated with the optimal dose of DMPP to assess the airway responsiveness.

Measurement of AHR

Airway hyper-reactivity (AHR) in response to metacholine was measured in anesthetized, tracheotomized, ventilated mice using a computer-controlled ventilator (FlexiVENT).

Figure 19:
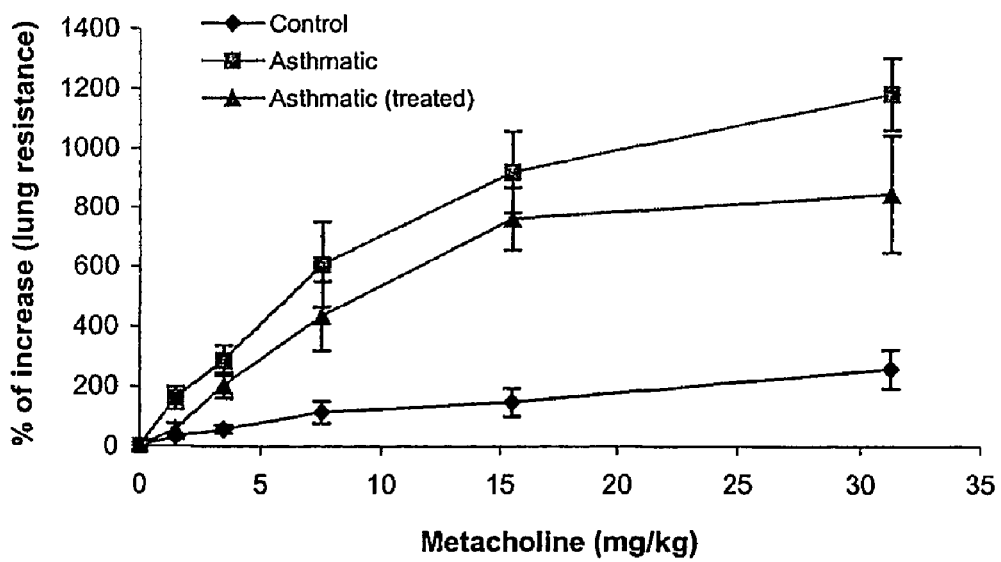
FIG. 19: Lung resistance after metacholine challenges from normal, asthmatic and asthmatic treated with 0.5 mg/kg intranasal DMPP. DMPP reduces the % of augmentation of lung resistance compared to asthmatic mice.
Figure 20:
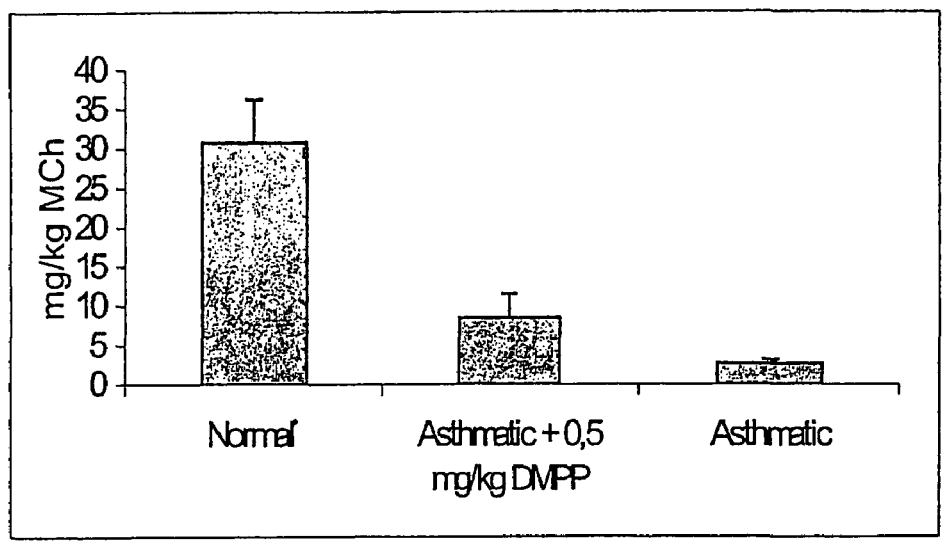
FIG. 20: The provocative challenge dose of 200% lung resistance augmentation (PC 200) was calculated. DMPP significantly reduced the PC200 in treated-mice compared to asthmatic mice (p=0.04; n=6).

Increasing doses of metacholine ((0 mg/kg-32.5 mg/kg) were administered through the jugular vein (FIGS. 19, 20).

Example 7

Effect of Agonist Treatment on mRNA Expression of IL-4

Figure 21:
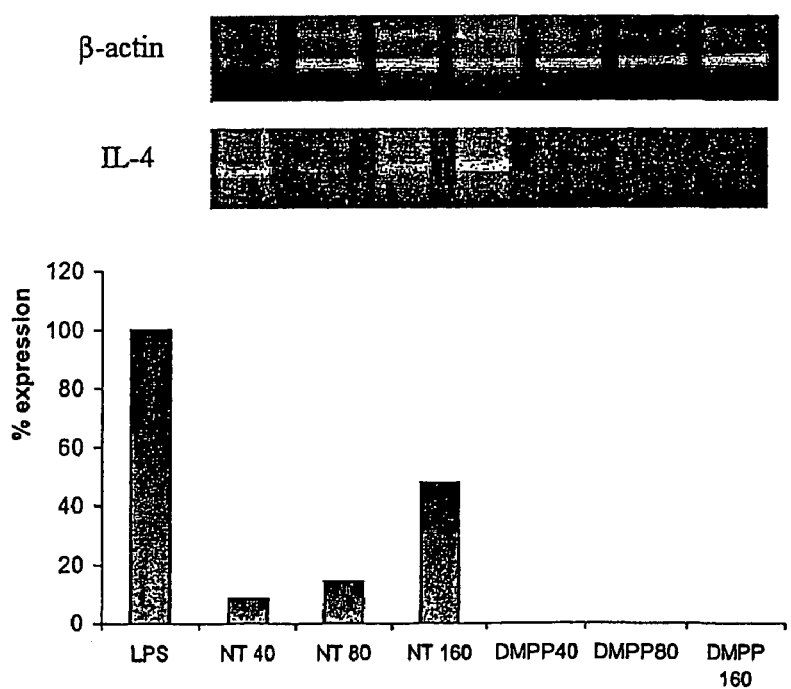
FIG. 21: IL-4 mRNA expression was induced by a 24 h LPS stimulation. Results are expressed as described in FIG. 3. Cells were treated with different doses (40 to 160 µM for both nicotine and DMPP). The nicotine treatment induced a drop in the IL-4 mRNA expression (up to a 90% reduction of expression in the 40 µM group). DMPP treatment completely blocked IL-4 mRNA expression in the LPS stimulated cells, at all doses.

The effect of agonist treatment on mRNA expression of IL-4, a cytokine that is well known to be involved in the development of asthma, was also tested (53). Nicotine decreased LPS-induced IL-4 mRNA expression by up to 92% with 40 μM DMPP completely blocked IL-4 mRNA expression (FIG. 21).

Example 8

Action of Various Agonists on Eosinophil Transmigration

To further investigate the effect of nicotinic agonists on the down-regulation of inflammation in asthma, we tested the action of various agonists on eosinophil transmigration.

Figure 22:
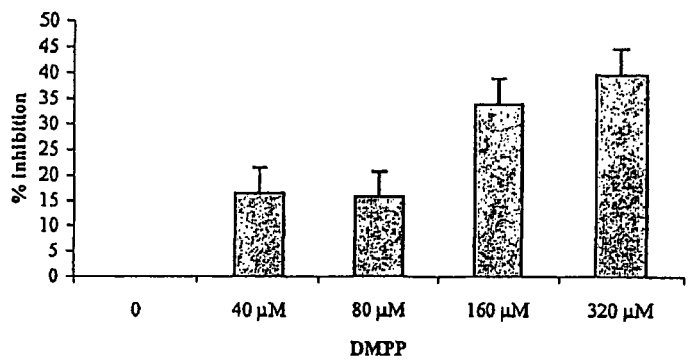
FIG. 22: Effect of DMPP on blood eosinophil transmigration. DMPP induces a dose-related inhibition of eosinophil transmigration across an artificial basement membrane.
Figure 23:
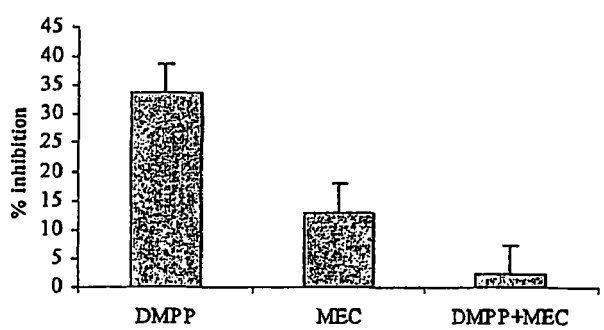
FIG. 23: Effect of mecamylamine, a nicotinic antagonist, on the inhibitory effect of DMPP on blood eosinophil transmigration. Mecamylamine reverses the effect of DMPP, suggesting that nicotinic receptor activation is necessary for the DMPP inhibitory effect.
Figure 24:
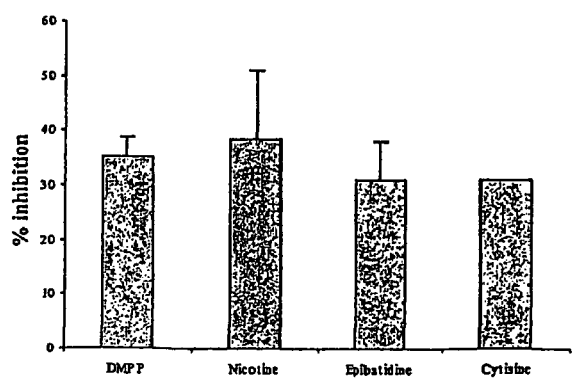
FIG. 24: Effect of other nicotinic agonists on transmigration of blood eosinophils. Nicotine, epibatidine and cytosine all reduce blood eosinophil transmigration.

Infiltration of eosinophils and other inflammatory cells into lung tissues is an important feature of asthma and the cause of airway inflammation and hyper-responsiveness. The passage of inflammatory cells from the circulation to the lung involves migration through the vascular endothelium, the basement membrane, and extra-cellular matrix components. Inflammatory cells cross the basement membrane by producing proteinases. In these preliminary in vitro experiments, we investigated the effects of various nicotinic agonists on the migration of purified blood eosinophils through an artificial basement membrane (Matrigel® coated chemotaxis chamber). DMPP induces a dose-related inhibition of eosinophils transmigration (FIG. 22), while this effect is reversed by the antagonist mecamylamine (MEC) (FIG. 23). This inhibitory effect is further confirmed with other nicotinic agonists including nicotine, epibatidine and cytosine (FIG. 24). Results are expressed as a percentage of inhibition (agonists-treated cells) compared to the control condition without the agonists.

These results suggest that nicotinic agonists down-regulate the synthesis or activation of proteinases that degrade basement membrane components, thus inhibiting the migration of eosinophils into lung mucosa.

Example 9

Effect of Nicotinic Agonists on Collagen Production

Asthma is characterized by airway structural changes, including sub-epithelial collagen deposition, that may be a cause for the chronicity of the disease. An imbalance between collagen synthesis and its degradation by fibroblasts may be involved in this process (56). In preliminary experiments, we investigated the effects of nicotinic agonists on collagen A1 synthesis produced by primary normal fibroblasts. Collagen A1 gene expression was evaluated by RT-PCR.

The results are expressed as percentage of gene expression in agonists treated cells compared to non-treated cells.

Figure 25:
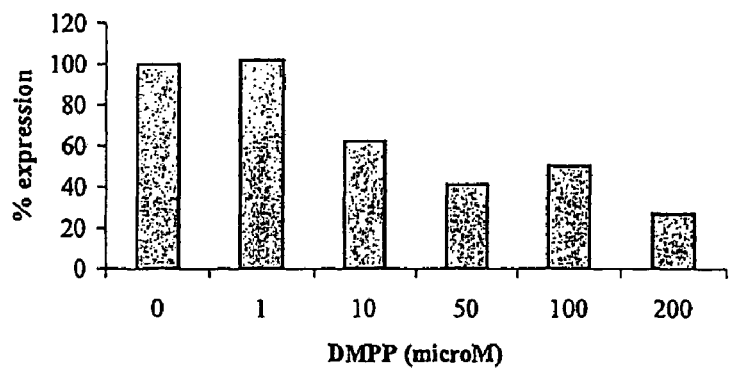
FIG. 25: Effect of DMPP on collagen 1A mRNA expression by normal human lung fibroblasts. DMPP inhibits collagen 1A mRNA expression in a dose dependant manner.
Figure 26:
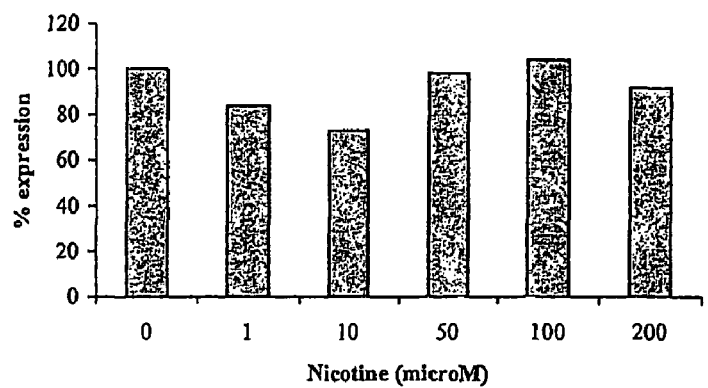
FIG. 26: Effect of nicotine on collagen 1A mRNA expression by human lung fibroblasts. Nicotine inhibits collagen 1A mRNA expression at 1 and 10 µM while the higher doses have no inhibitory effect.
Figure 27:
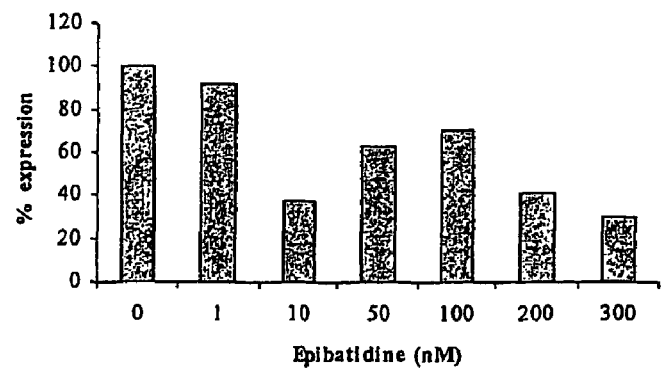
FIG. 27: Effect of epibatidine, another nicotinic agonist, on collagen 1A mRNA expression by human lung fibroblasts. Epibatidine also has an inhibitory effect on collagen 1A mRNA expression.

DMPP inhibits collagen A1 gene expression in a dose-dependant manner (FIG. 25). Nicotine has a slight inhibitory effect at 1 and 10 μM, whereas higher concentrations had no effects (FIG. 26), probably due to a desensitization of the receptors. Lower doses may be necessary to achieve an inhibition and will be tested. The inhibitory effect is also observed with epibatidine (FIG. 27).

Although the present invention has been described hereinabove by way of preferred embodiments thereof, it can be modified, without departing from the spirit and nature of the subject invention as defined in the appended claims.

REFERENCES

1. Cormier, Y., J. Belanger, and P. Durand. 1985. Factors influencing the development of serum precipitins to farmer's lung antigen in Quebec dairy farmers. *Thorax* 40 (2): 138-42.
2. Cormier, Y., L. Gagnon, F. Berube-Genest, and M. Fournier. 1988. Sequential bronchoalveolar lavage in experimental extrinsic allergic alveolitis. The influence of cigarette smoking. Am Rev Respir Dis 137(5): 1104-9.
3. Cormier, Y., E. Israel-Assayag, G. Bedard, and C. Duchaine. 1998. Hypersensitivity pneumonitis in peat moss processing plant workers. Am J Respir Crit Care Med 158(2): 412-7.
4. Gariepy, L., Y. Cormier, M. Laviolette, and A. Tardif. 1989. redictive value of bronchoalveolar lavage cells and serum precipitins in asymptomatic dairy farmers. Am Rev Respir Dis 140(5):1386-9.
5. Lawrence, E. C., T. B. Fox, R. B. Teague, K. Bloom, and R. K. Wilson. 1986. Cigarette smoking and bronchoalveolar T cell populations in sarcoidosis. Ann N Y Acad Sci 465:657-64.
6. Valeyre, D., P. Soler, C. Clerici, J. Pre, J. P. Battesti, R. Georges, and A. J. Hance. 1988. Smoking and pulmonary sarcoidosis: effect of cigarette smoking on prevalence, clinical manifestations, alveolitis, and evolution of the disease. Thorax 43(7):516-24.
7. Rubin, D. T., and S. B. Hanauer. 2000. Smoking and inflammatory bowel disease. Eur J Gastroenterol Hepatol 12(8):855-62.
8. Thomas, G. A., J. Rhodes, J. T. Green, and C. Richardson. 2000. Role of smoking in inflammatory bowel disease: implications for therapy. Postgrad Med J 76(895):273-9.
9. Guslandi, M. 1999. Nicotine treatment for ulcerative colitis. Br J Clin Pharmacol 48(4):481-4.
10. Guslandi, M. 1999. Long-term effects of a single course of nicotine treatment in acute ulcerative colitis: remission maintenance in a 12-month follow-up study. Int J Colorectal Dis 14(4-5):261-2.
11. Rezvani, A. H., and E. D. Levin. 2001. Cognitive effects of nicotine. Biol Psychiatry 49(3):258-67.
12. Kelton, M. C., H. J. Kahn, C. L. Conrath, and P. A. Newhouse. 2000. The effects of nicotine on Parkinson's disease. Brain Cogn 43(1-3):274-82.
13. Bertram, K. G. 1998. Basic and clinical pharmacology. Editions Appelton and Lange. Stanford, Conn.
14. Sekhon, H. S., Y. Jia, R. Raab, A. Kuryatov, J. F. Pankow, J. A. Whitsett, J. Lindstrom, and E. R. Spindel. 1999. Prenatal nicotine increases pulmonary alpha7 nicotinic receptor expression and alters fetal lung development in monkeys. J Clin Invest 103(5):637-47.
15. Maus, A. D., E. F. Pereira, P. I. Karachunski, R. M. Horton, D. Navaneetham, K. Macklin, W. S. Cortes, E. X. Albuquerque, and B. M. Conti-Fine. 1998. Human and rodent bronchial epithelial cells express functional nicotinic acetylcholine receptors. Mol Pharmacol 54(5):779-88.
16. Shriver, S. P., H. A. Bourdeau, C. T. Gubish, D. L. Tirpak, A. L. Davis, J. D. Luketich, and J. M. Siegfried. 2000. Sex-specific expression of gastrin-releasing peptide receptor: relationship to smoking history and risk of lung cancer. J Natl Cancer Inst 92(1):24-33.

17. Ferguson, D. G., M. A. Haxhiu, A. J. To, B. Erokwu, and I. A. Dreshaj. 2000. The alpha3 subtype of the nicotinic acetylcholine receptor is expressed in airway-related neurons of the nucleus tractus solitarius, but is not essential for reflex bronchoconstriction in ferrets. Neurosci Lett 287(2): 141-5.
18. Singh, S. P., R. Kalra, P. Puttfarcken, A. Kozak, J. Tesfaigzi, and M. L. Sopori. 2000. Acute and chronic nicotine exposures modulate the immune system through different pathways. Toxicol Appl Pharmacol 164(1):65-72.
19. Kalra, R., S. P. Singh, S. M. Savage, G. L. Finch, and M. L. Sopori. 2000. Effects of cigarette smoke on immune response: chronic exposure to cigarette smoke impairs antigen-mediated signaling in T cells and depletes IP3-sensitive Ca(2+) stores. J Pharmacol Exp Ther 293(1):166-71.
20. Sugano, N., K. Shimada, K. Ito, and S. Murai. 1998. Nicotine inhibits the production of inflammatory mediators in U937 cells through modulation of nuclear factor-kappaB activation. Biochem Biophys Res Commun 252 (1):25-8.
21. Yates, S. L., M. Bencherif, E. N. Fluhler, and P. M. Lippiello. 1995. Up-regulation of nicotinic acetylcholine receptors following chronic exposure of rats to mainstream cigarette smoke or alpha 4 beta 2 receptors to nicotine. Biochem Pharmacol 50(12):2001-8.
22. Sopori, M. L., and W. Kozak. 1998. Immunomodulatory effects of cigarette smoke. J Neuroimmunol 83(1-2):148-56.
23. Lahmouzi, J., F. Simain-Sato, M. P. Defresne, M. C. De Pauw, E. Heinen, T. Grisar, J. J. Legros, and R. Legrand. 2000. Effect of nicotine on rat gingival fibroblasts in vitro. Connect Tissue Res 41(1):69-80.
24. Geng, Y., S. M. Savage, S. Razanai-Boroujerdi, and M. L. Sopori. 1996. Effects of nicotine on the immune response. II. Chronic nicotine treatment induces T cell anergy. J Immunol 156(7):2384-90.
25. McCrea, K. A., J. E. Ensor, K. Nall, E. R. Bleecker, and J. D. Hasday. 1994. Altered cytokine regulation in the lungs of cigarette smokers. Am J Respir Crit Care Med 150(3): 696-703.
26. Ohta, T., N. Yamashita, M. Maruyama, E. Sugiyama, and M. Kobayashi. 1998. Cigarette smoking decreases interleukin-8 secretion by human alveolar macrophages. Respir Med 92(7):922-7.
27. Suzuki, N., S. Wakisaka, Y. Takeba, S. Mihara, and T. Sakane. 1999. Effects of cigarette smoking on Fas/Fas ligand expression of human lymphocytes. Cell Immunol 192(1):48-53.
28. Zia, S., A. Ndoye, V. T. Nguyen, and S. A. Grando. 1997. Nicotine enhances expression of the alpha 3, alpha 4, alpha 5, and alpha 7 nicotinic receptors modulating calcium metabolism and regulating adhesion and motility of respiratory epithelial cells. Res Commun Mol Pathol Pharmacol 97(3):243-62.
29. Zhang, S., and T. M. Petro. 1996. The effect of nicotine on murine CD4 T cell responses. Int J Immunopharmacol 18(8-9):467-78.
30. Bugeon, L., and M. J. Dallman. 2000. Costimulation of T cells. Am J Respir Crit Care Med 162(4 Pt 2):S164-8.
31. Green, J. M. 2000. The B7/CD28/CTLA4 T-cell activation pathway. Implications for inflammatory lung disease. Am J Respir Cell Mol Biol 22(3):261-4.
32. Lenschow, D. J., T. L. Walunas, and J. A. Bluestone. 1996. CD28/B7 system of T cell costimulation. Annu Rev Immunol 14:233-58.
33. Walunas, T. L., and J. A. Bluestone. 1998. CTLA-4 regulates tolerance induction and T cell differentiation in vivo. J Immunol 160(8):3855-60.
34. Walunas, T. L., D. J. Lenschow, C. Y. Bakker, P. S. Linsley, G. J. Freeman, J. M. Green, C. B. Thompson, and J. A. Bluestone. 1994. CTLA-4 can function as a negative regulator of T cell activation. Immunity 1(5):405-13.
35. Israel-Assayag, E., A. Dakhama, S. Lavigne, M. Laviolette, and Y. Cormier. 1999. Expression of costimulatory molecules on alveolar macrophages in hypersensitivity pneumonitis. Am J Respir Crit Care Med 159(6):1830-4.
36. Israel-Assayag, E., M. Fournier, and Y. Cormier. 1999. Blockade of T cell costimulation by CTLA4-Ig inhibits lung inflammation in murine hypersensitivity pneumonitis. J Immunol 163(12):6794-9.
37. Larche, M., S. J. Till, B. M. Haselden, J. North, J. Barkans, C. J. Corrigan, A. B. Kay, and D. S. Robinson. 1998. Costimulation through CD86 is involved in airway antigen-presenting cell and T cell responses to allergen in atopic asthmatics. J Immunol 161(11):6375-82.
38. Mathur, M., K. Herrmann, Y. Qin, F. Gulmen, X. Li, R. Krimins, J. Weinstock, D. Elliott, J. A. Bluestone, and P. Padrid. 1999. CD28 interactions with either CD80 or CD86 are sufficient to induce allergic airway inflammation in mice. Am J Respir Cell Mol Biol 21 (4):498-509.
39. Nicod, L. P., and P. Isler. 1997. Alveolar macrophages in sarcoidosis coexpress high levels of CD86 (B7.2), CD40, and CD30L. Am J Respir Cell Mol Biol 17(1):91-6.
40. Kesingland, A. C., C. T. Gentry, M. S. Panesar, M. A. Bowes, J. M. Vernier, R. Cube, K. Walker, and L. Urban. 2000. Analgesic profile of the nicotinic acetylcholine receptor agonists, (+)-epibatidine and ABT-594 in models of persistent inflammatory and neuropathic pain. Pain 86(1-2):113-8.
41. Mellon, R. D., and B. M. Bayer. 1999. The effects of morphine, nicotine and epibatidine on lymphocyte activity and hypothalamic-pituitary-adrenal axis responses. J Pharmacol Exp Ther 288(2):63542.
42. Yokotani, K., M. Wang, S. Okada, Y. Murakami, and M. Hirata. 2000. Characterization of nicotinic acetylcholine receptor-mediated noradrenaline release from the isolated rat stomach. Eur J Pharmacol 402(3):223-9.
43. Yost, C. S., and B. D. Winegar. 1997. Potency of agonists and competitive antagonists on adult- and fetal-type nicotinic acetylcholine receptors. Cell Mol Neurobiol 17(1): 35-50.
44. Fecho, K., K. A. Maslonek, L. A. Dykstra, and D. T. Lysle. 1993. Alterations of immune status induced by the sympathetic nervous system: immunomodulatory effects of DMPP alone and in combination with morphine. Brain Behav Immun 7(3):253-70.
45. Thompson, D. C., R. J. Altiere, and L. Diamond. 1990. Nicotinic agonist modulation of feline bronchomotor tone. Clin Exp Pharmacol Physiol 17(2):83-97.
46. Barnes P J. 2001. Future Advances in COPD Therapy. Respiration 68(5):441-8.
47. Lasky J A and Ortiz, L A. 2001. Antifibrotic therapy for the treatment of pulmonary fibrosis. Am J Med Sci 322(4): 213-21.
48. Baron, J. A. 1996. Beneficial effects of nicotine and cigarette smoking: the real, the possible and the spurious. Br Med Bull 52(1):58-73.
49. Waldum, H. L., O. G. Nilsen, T. Nilsen, H. Rorvik, V. Syversen, A. K. Sanvik, O. A. Haugen, S. H. Torp, and E. Brenna. 1996. Long-term effects of inhaled nicotine. Life Sci 58(16):1339-46.

50. Warren, C. P. 1977. Extrinsic allergic alveolitis: a disease commoner in non-smokers. Thorax 32(5):567-9.
51. Cormier, Y., G. M. Tremblay, M. Fournier, and E. Israel-Assayag. 1994. Long-term viral enhancement of lung response to *Saccharopolyspora rectivirgula*. Am J Respir Crit Care Med 149(2 Pt 1):4904.
52. Gudmundsson, G., and G. W. Hunninghake. 1997. Interferon-gamma is necessary for the expression of hypersensitivity pneumonitis. J Clin Invest 99(10):2386-90.
53. Denis, M., M. Bedard, M. Laviolette, and Y. Cormier. 1993. A study of monokine release and natural killer activity in the bronchoalveolar lavage of subjects with farmer's lung. Am Rev Respir Dis 147(4):934-9.
54. Wahlstrom, J., K. Katchar, H. Wigzell, O. Olerup, A. Eklund, and J. Grunewald. 2001. Analysis of intracellular cytokines in cd4(+) and cd8(+) lung and blood t cells in sarcoidosis. Am J Respir Crit Care Med 163(1):115-21.
55. Cohn, L., C. Herrick, N. Niu, R. Homer, and K. Bottomly. 2001. IL-4 promotes airway eosinophilia by suppressing IFN-gamma production: defining a novel role for IFN-gamma in the regulation of allergic airway inflammation. J Immunol 166(4):2760-7.
56. Laliberte R., Rouabhia M, Bosse M, Chakir J. 2001 Decreased capacity of asthmatic bronchial fibroblasts to degrade collagen. Matrix Biol Jan; 19(8):743-53.
57. Boulet, L. P., H. Turcotte, M. Laviolette, F. Naud, M. C. Bernier, S. Martel, and J. Chakir. 2000. Airway hyperresponsiveness, inflammation, and subepithelial collagen deposition in recently diagnosed versus long-standing mild asthma. Influence of inhaled corticosteroids. Am J Respir Crit Care Med 162(4 Pt 1):1308-13.
58. Dempsey, O. J. 2000. Leukotriene receptor antagonist therapy. Postgrad Med J 76(902):767-73.
59. Busse, W. W. 1998. Leukotrienes and inflammation. Am J Respir Crit Care Med 157(6 Pt 2):S210-3; discussion S247-8.
60. Zisman, D. A., J. P. Lynch, G. B. Toews, E. A. Kazerooni, A. Flint, and F. J. Martinez. 2000. Cyclophosphamide in the treatment of idiopathic pulmonary fibrosis: a prospective study in patients who failed to respond to corticosteroids. Chest 117(6):1619-26.
61. Redington, A. E. 2000. Fibrosis and airway remodelling. Clin Exp Allergy 30 Suppl 1:42-5.
62. Frew, A. J., and Plummeridge M J. 2001. Alternative agents in asthma. J Allergy Clin Immunol 108(1):3-10.

What is claimed is:

1. A method of treating pulmonary inflammation of an inflammatory disease selected from the group consisting of asthma, interstitial pulmonary fibrosis (IPF), sarcoidosis, hypersensitivity pneumonitis (HP), chronic HP and bronchiolitis obliterans with organizing pneumonitis (BOOP) in an animal in need thereof having said inflammation, comprising administering to said animal a nicotinic receptors agonist selected from epibatidine.

2. The method as defined in claim 1, wherein said pulmonary inflammatory disease is asthma.

3. The method as defined in claim 1, wherein said nicotinic receptors agonist is administered by oral, sublingual, intraperitoneal, intravenous, inhaled, intratracheal, intranasal, parenteral, topical, direct injection, infusion or intraocular administration.

4. The method as defined in claim 2, further comprising administering at least one of bronchodilator, anti-inflammatory, antileukotriene or immunosuppressive agent.

5. The method as defined in claim 4, wherein said at least one of bronchodilator, anti-inflammatory, antileukotriene or immunosuppressive agent is administered by oral, sublingual, intraperitoneal, intravenous, inhaled, intratracheal, intranasal, parenteral, topical, direct injection, infusion or intraocular administration.

6. A method of treating bronchial or interstital inflammation from a pulmonary-inflammatory disease selected from the group consisting of asthma, interstitial pulmonary fibrosis (IPF), sarcoidosis, hypersensitivity pneumonitis (HP), chronic HP and bronchiolitis obliterans with organizing pneumonitis (BOOP) in an animal in need thereof having said inflammation, comprising administering to said animal a nicotinic receptors agonist selected from epibatidine.

7. The method as defined in claim 6, wherein said pulmonary inflammatory disease is asthma.

* * * * *

UNITED STATES PATENT AND TRADEMARK OFFICE
CERTIFICATE OF CORRECTION

PATENT NO. : 7,601,720 B2  Page 1 of 1
APPLICATION NO. : 10/469999
DATED : October 13, 2009
INVENTOR(S) : Cormier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1097 days.

Signed and Sealed this

Fifth Day of October, 2010

David J. Kappos
*Director of the United States Patent and Trademark Office*